US011490893B2

(12) United States Patent
Marczyk et al.

(10) Patent No.: US 11,490,893 B2
(45) Date of Patent: Nov. 8, 2022

(54) ENDOSCOPIC STAPLER AND STAPLE

(71) Applicant: Covidien LP, Mansfield, MA (US)

(72) Inventors: Stanislaw Marczyk, Stratford, CT (US); Ernie Aranyi, Easton, CT (US); Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 250 days.

(21) Appl. No.: 16/720,695

(22) Filed: Dec. 19, 2019

(65) Prior Publication Data

US 2020/0121320 A1  Apr. 23, 2020

Related U.S. Application Data

(62) Division of application No. 14/803,249, filed on Jul. 20, 2015, now Pat. No. 10,548,599.

(51) Int. Cl.
*A61B 17/10* (2006.01)
*A61B 17/068* (2006.01)
*A61B 17/064* (2006.01)
*A61B 17/072* (2006.01)

(52) U.S. Cl.
CPC .......... *A61B 17/105* (2013.01); *A61B 17/068* (2013.01); *A61B 17/0644* (2013.01); *A61B 17/072* (2013.01); *A61B 2017/07228* (2013.01); *A61B 2017/07278* (2013.01)

(58) Field of Classification Search
CPC ... A61B 17/105; A61B 17/068; A61B 17/064; A61B 2017/07278
USPC ............................................... 227/177, 176.1
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

Japanese Office Action dated Jan. 14, 2021, issued in corresponding Japanese Appln. No. 2016137395, 3 pages.

(Continued)

*Primary Examiner* — Andrew M Tecco
*Assistant Examiner* — Nicholas E Igbokwe

(57) ABSTRACT

A surgical stapler has a tool assembly including an anvil and a staple cartridge having a series of staples which are supported and configured to be rotatably ejected from the staple cartridge into the anvil to suture tissue. In embodiments, the surgical stapler includes a cartridge that supports a plurality of rotatable pushers. Each pusher supports a curved, substantially U-shaped staple having a single tissue penetrating distal leg portion and a proximal leg portion. The pusher is rotatable to drive the distal leg portion into an anvil to deform the staple into a substantially D-shaped configuration.

19 Claims, 23 Drawing Sheets

(56) References Cited

U.S. PATENT DOCUMENTS

| | | |
|---|---|---|
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Mien et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Fates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Ley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |

(56) References Cited

U.S. PATENT DOCUMENTS

| | | |
|---|---|---|
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |

(56) References Cited

U.S. PATENT DOCUMENTS

| | | |
|---|---|---|
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |

(56) References Cited

U.S. PATENT DOCUMENTS

| | | | |
|---|---|---|---|
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |

(56) References Cited

U.S. PATENT DOCUMENTS

| | | | |
|---|---|---|---|
| 7,950,561 | B2 | 5/2011 | Aranyi |
| 7,950,562 | B2 | 5/2011 | Beardsley et al. |
| 7,954,682 | B2 | 6/2011 | Giordano et al. |
| 7,954,683 | B1 | 6/2011 | Knodel et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,959,051 | B2 | 6/2011 | Smith et al. |
| 7,963,431 | B2 | 6/2011 | Scirica |
| 7,963,432 | B2 | 6/2011 | Knodel et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,975,894 | B2 | 7/2011 | Boyden et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,036 | B1 | 12/2011 | Knodel |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,261,958 | B1 * | 9/2012 | Knodel ............. A61B 17/064 227/176.1 |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |
| 8,276,594 | B2 | 10/2012 | Shah |
| 8,276,801 | B2 | 10/2012 | Zemlok et al. |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |

(56) References Cited

U.S. PATENT DOCUMENTS

| | | | |
|---|---|---|---|
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 * | 11/2013 | Shelton, IV ..... A61B 17/07207 227/176.1 |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |

(56) References Cited

U.S. PATENT DOCUMENTS

| | | |
|---|---|---|
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,369 B1 | 3/2014 | Manoux et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 9,655,613 B2 | 5/2017 | Schaller |
| 10,548,599 B2 | 2/2020 | Marczyk et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1* | 2/2011 | Zemlok ............ A61B 17/07207 227/175.1 |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |

(56) References Cited

U.S. PATENT DOCUMENTS

| | | |
|---|---|---|
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295270 A1 | 12/2011 | Giordano et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199630 A1 | 8/2012 | Shelton, IV |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Fates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0168431 A1 | 7/2013 | Zemlok et al. |

(56) References Cited

U.S. PATENT DOCUMENTS

| | | | | |
|---|---|---|---|---|
| 2014/0263546 | A1* | 9/2014 | Aranyi | A61B 17/07207 227/175.2 |
| 2015/0173748 | A1* | 6/2015 | Marczyk | A61B 17/068 227/177.1 |
| 2015/0230793 | A1* | 8/2015 | Kostrzewski | A61B 17/0684 227/176.1 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2891460 A1 | 7/2015 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2011083618 A | 4/2011 |
| SU | 659146 A1 | 4/1979 |
| SU | 728848 A1 | 4/1980 |
| SU | 980703 A1 | 12/1982 |
| SU | 390220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |
| WO | 2014175894 A1 | 10/2014 |

OTHER PUBLICATIONS

Partial European Search Report dated Nov. 18, 2016, issued in EP Application No. 16180073.
European Search Report dated Mar. 3, 2017, issued in EP Application No. 16180073.
Australian Examination Report dated Apr. 1, 2020, issued in AU Appln. No. 2016204293, 3 pages.
Japanese Office Action dated Sep. 1, 2020, issued in JP Appln. No. 2016-137395, 5 pages.

* cited by examiner

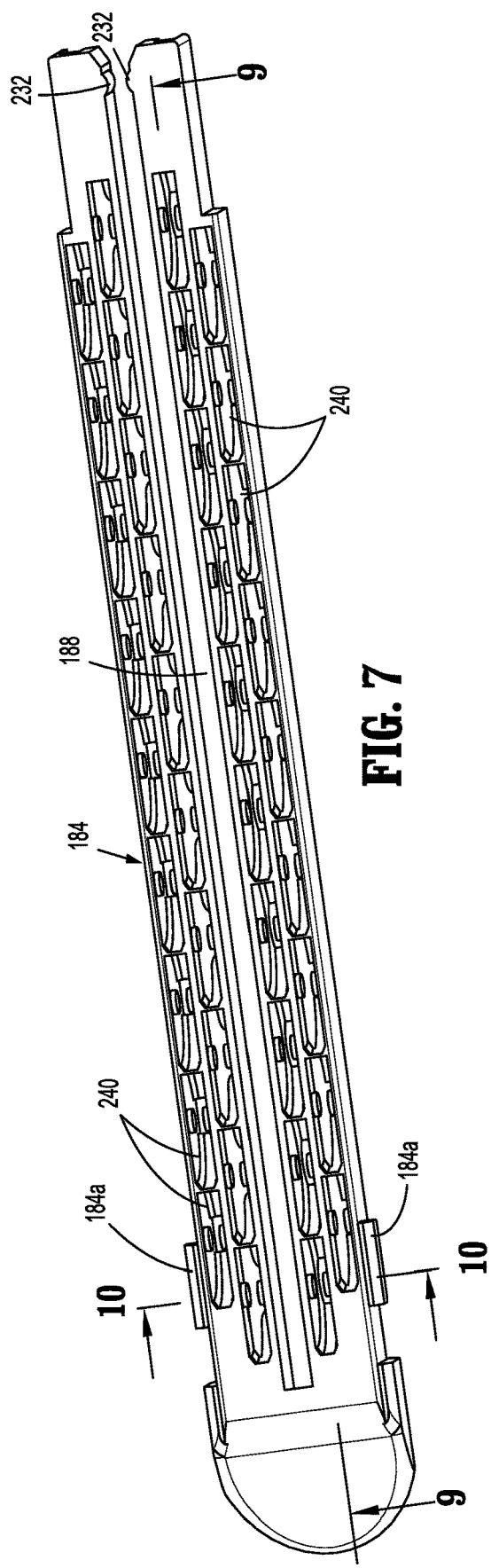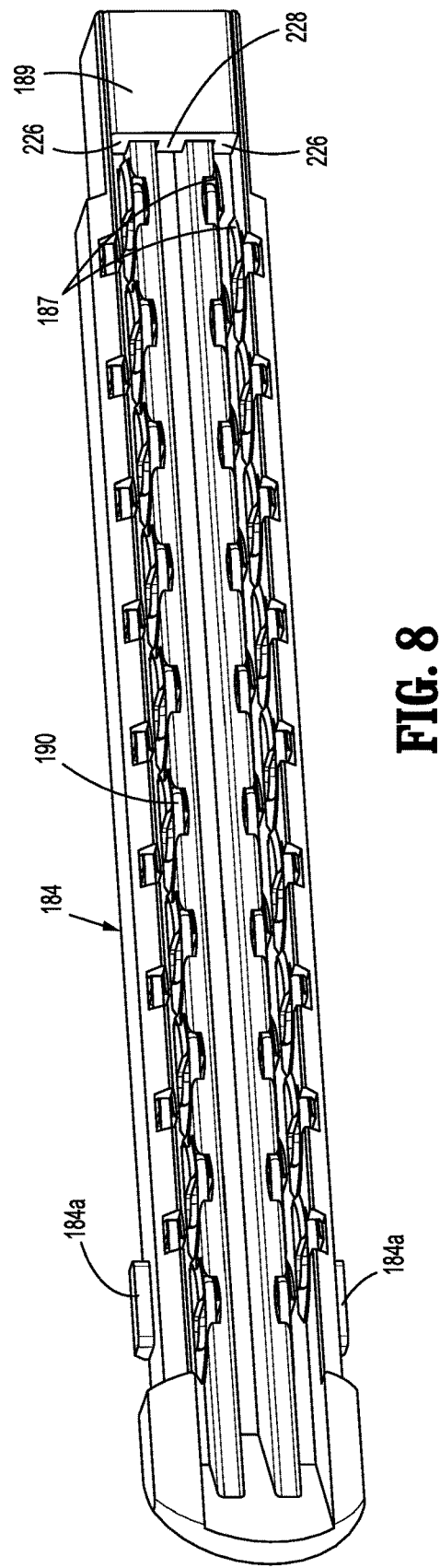

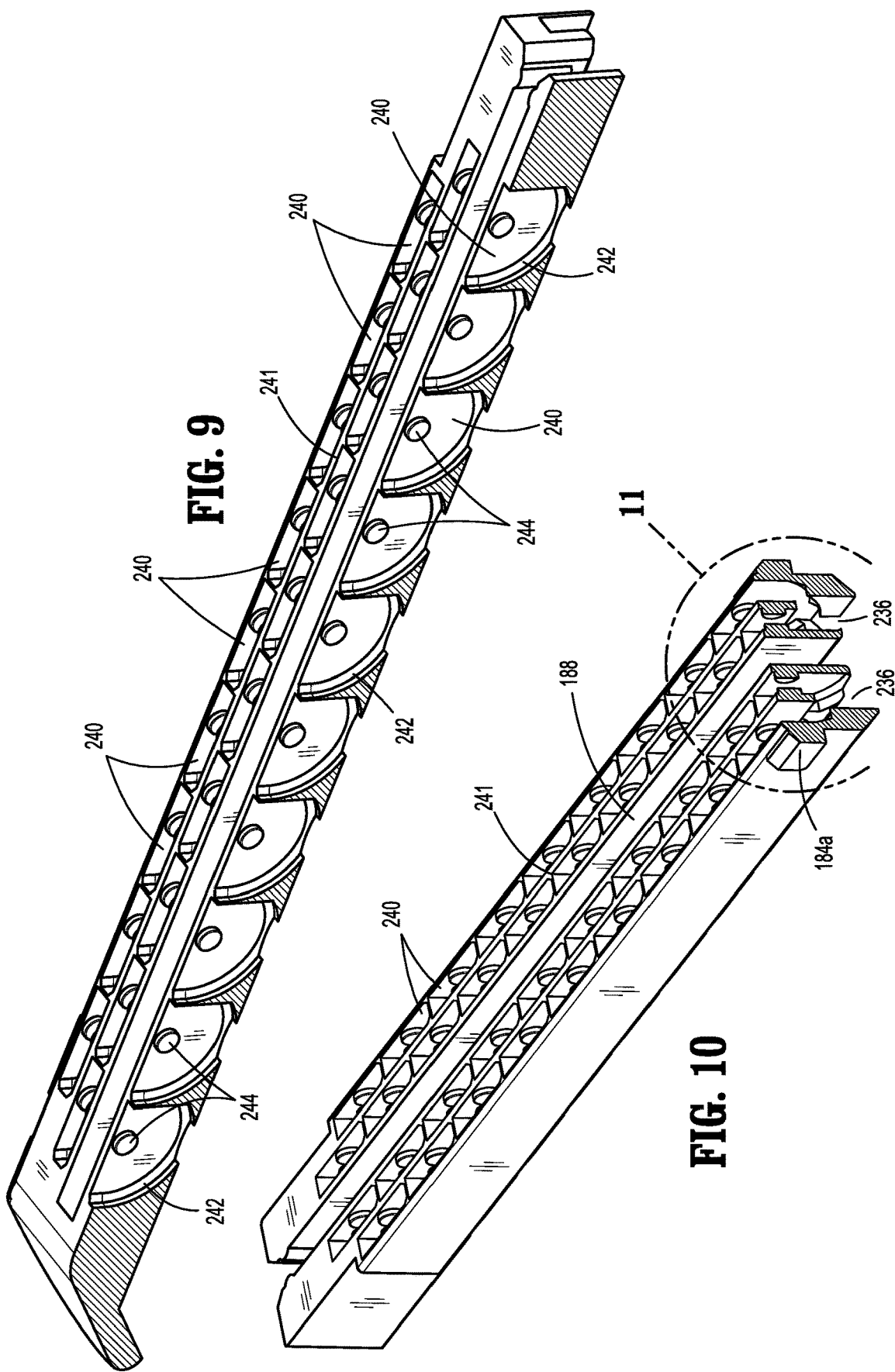

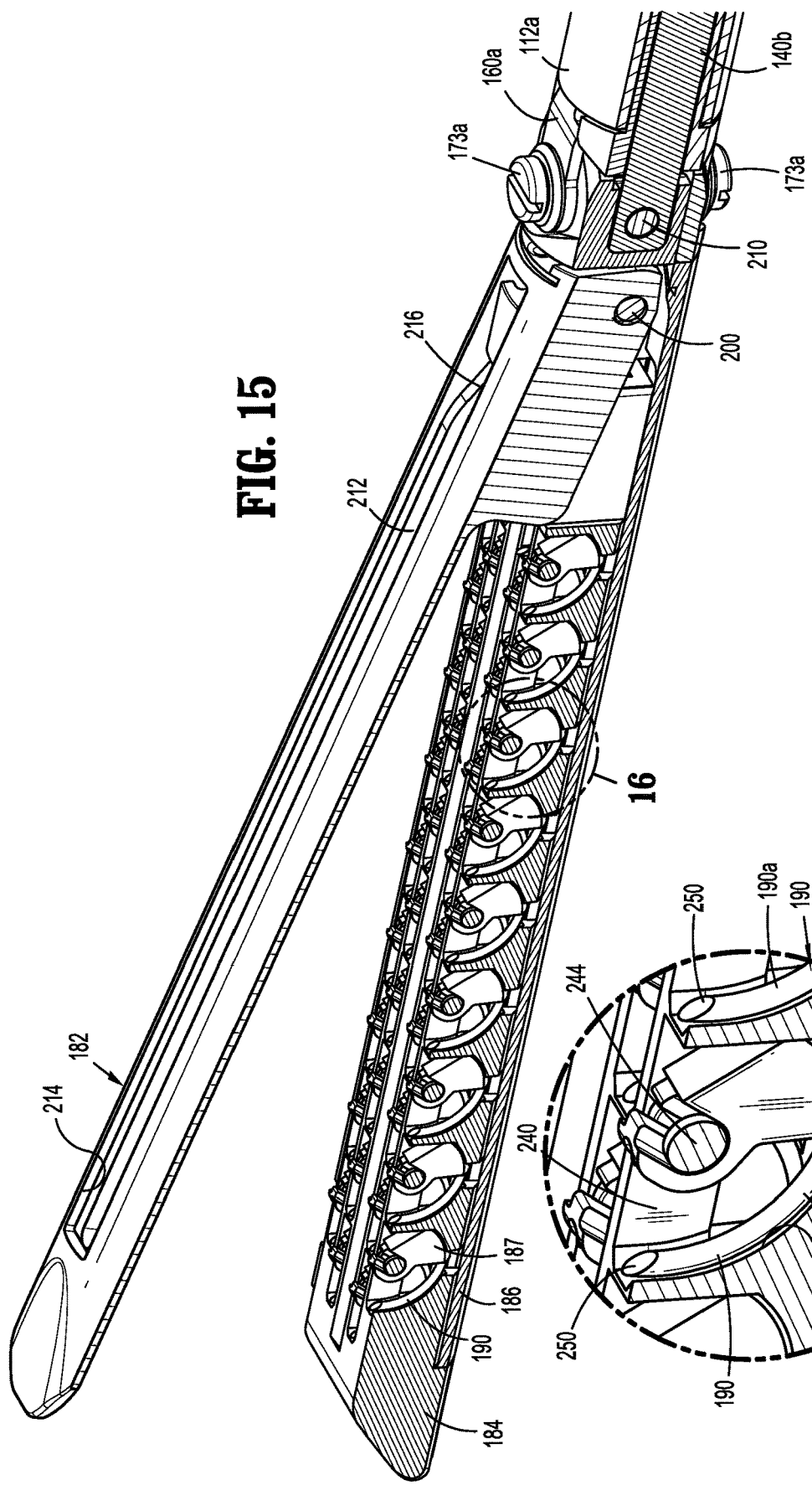
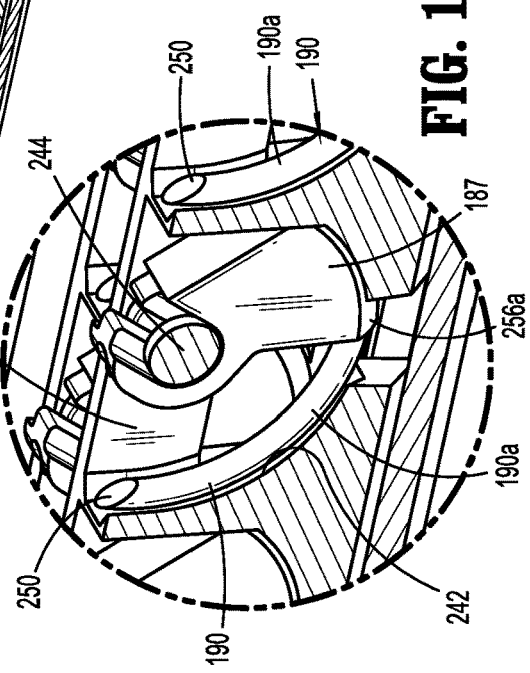
FIG. 15
FIG. 16

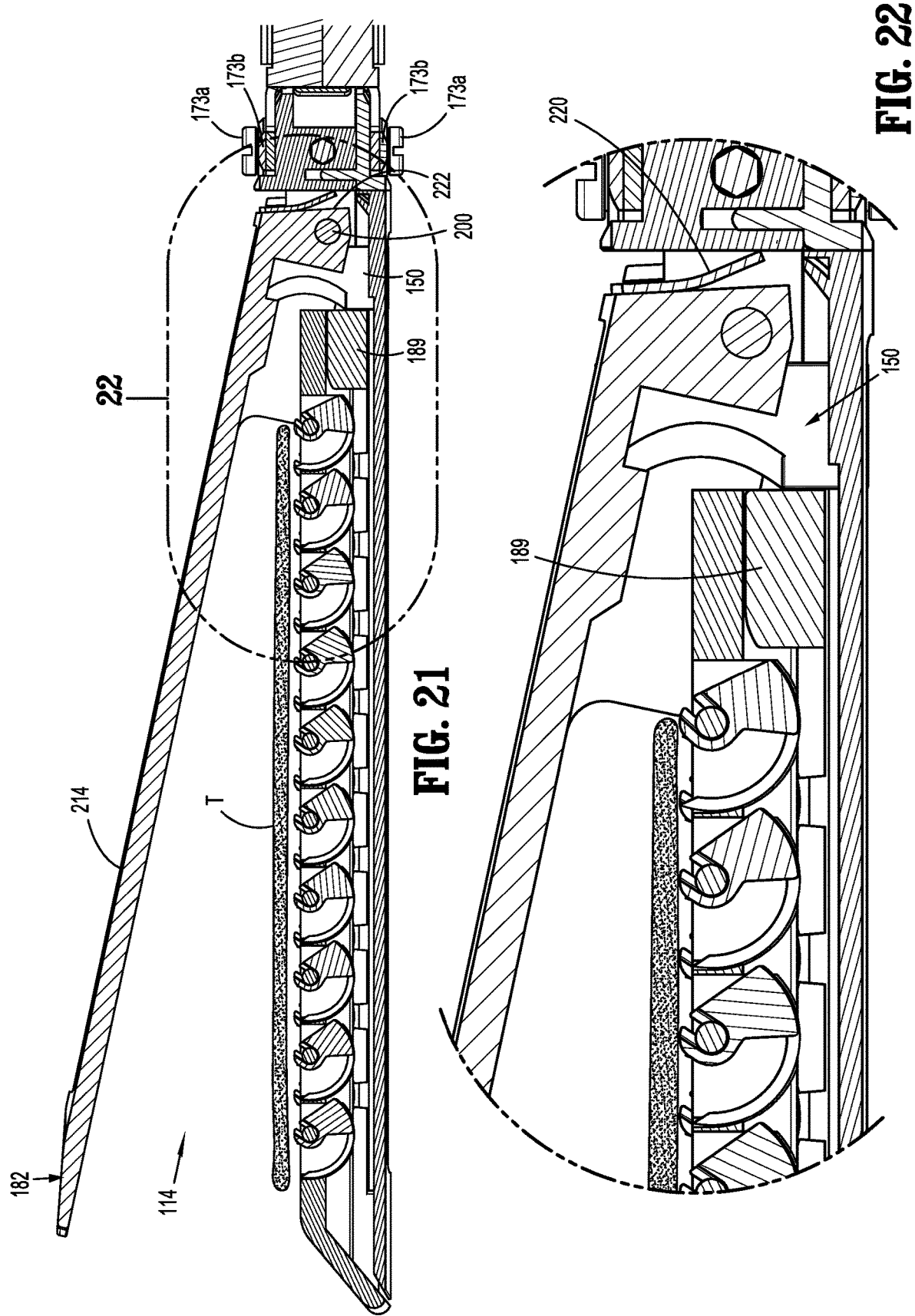

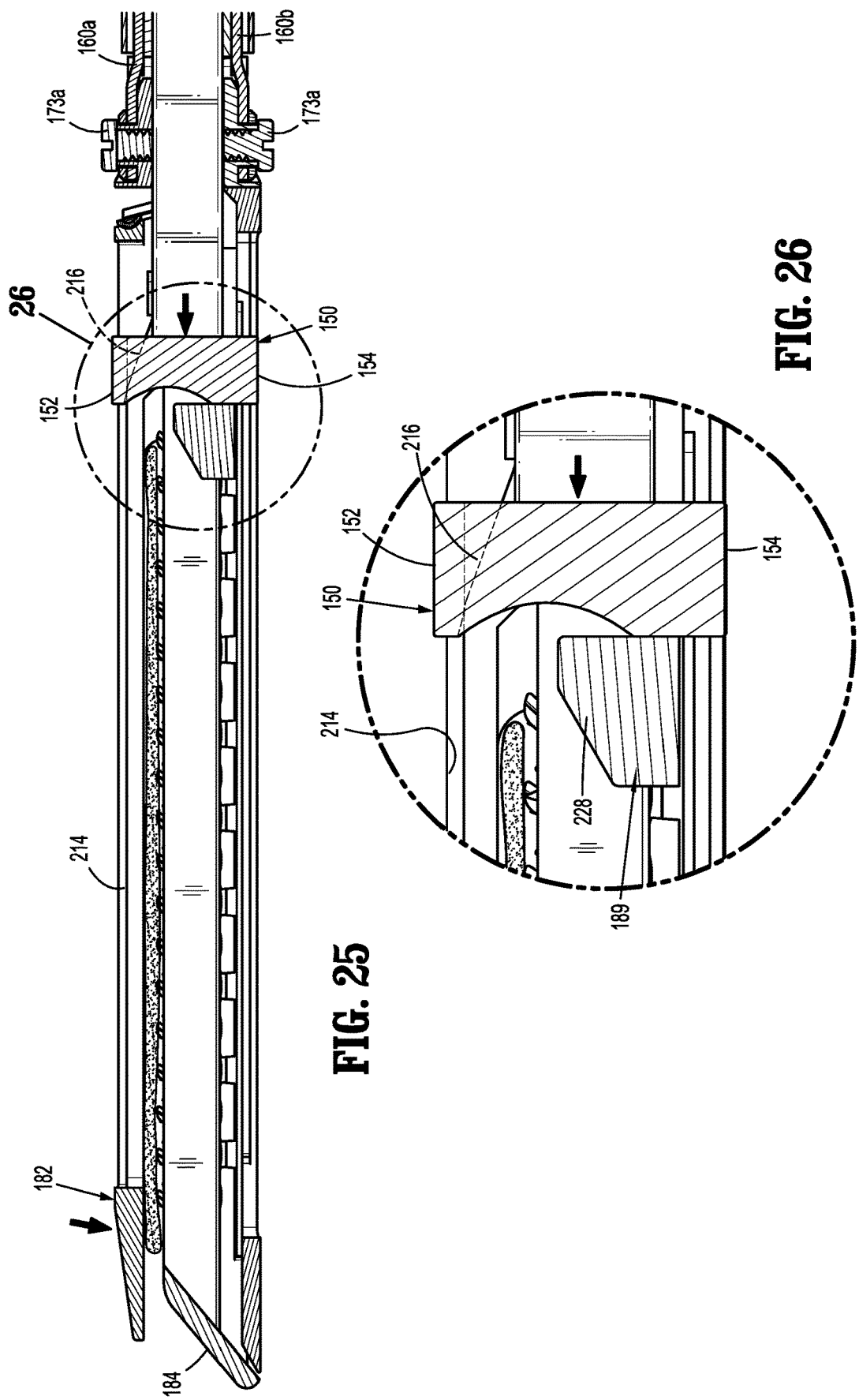

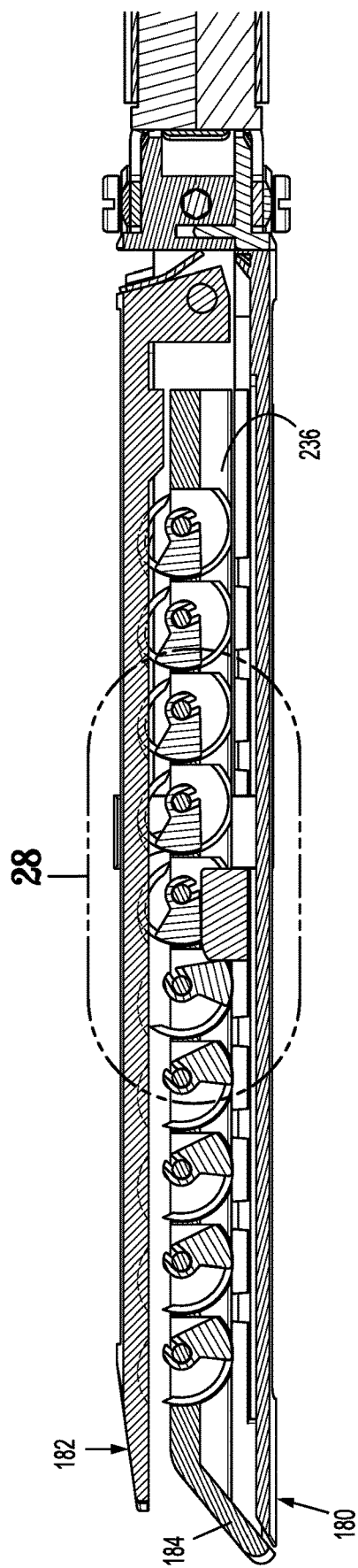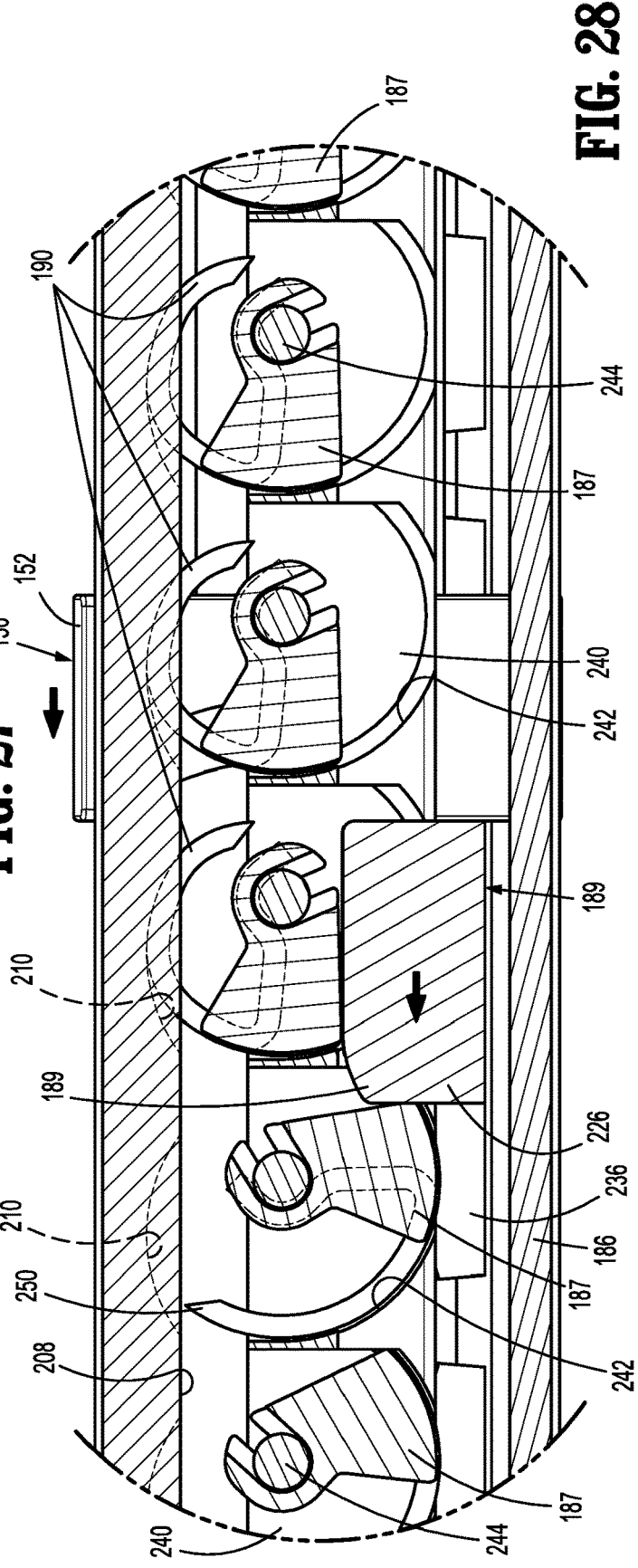

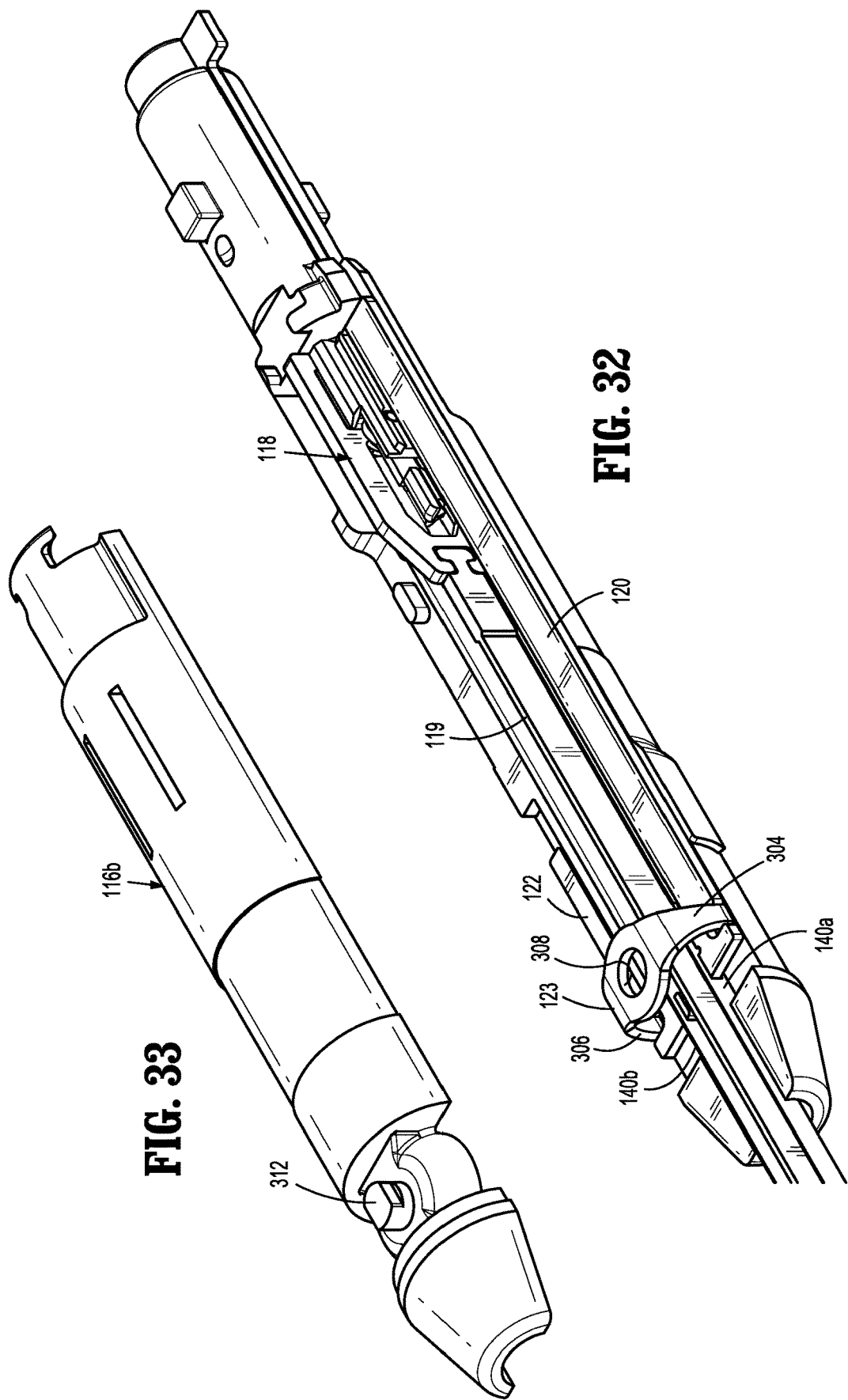

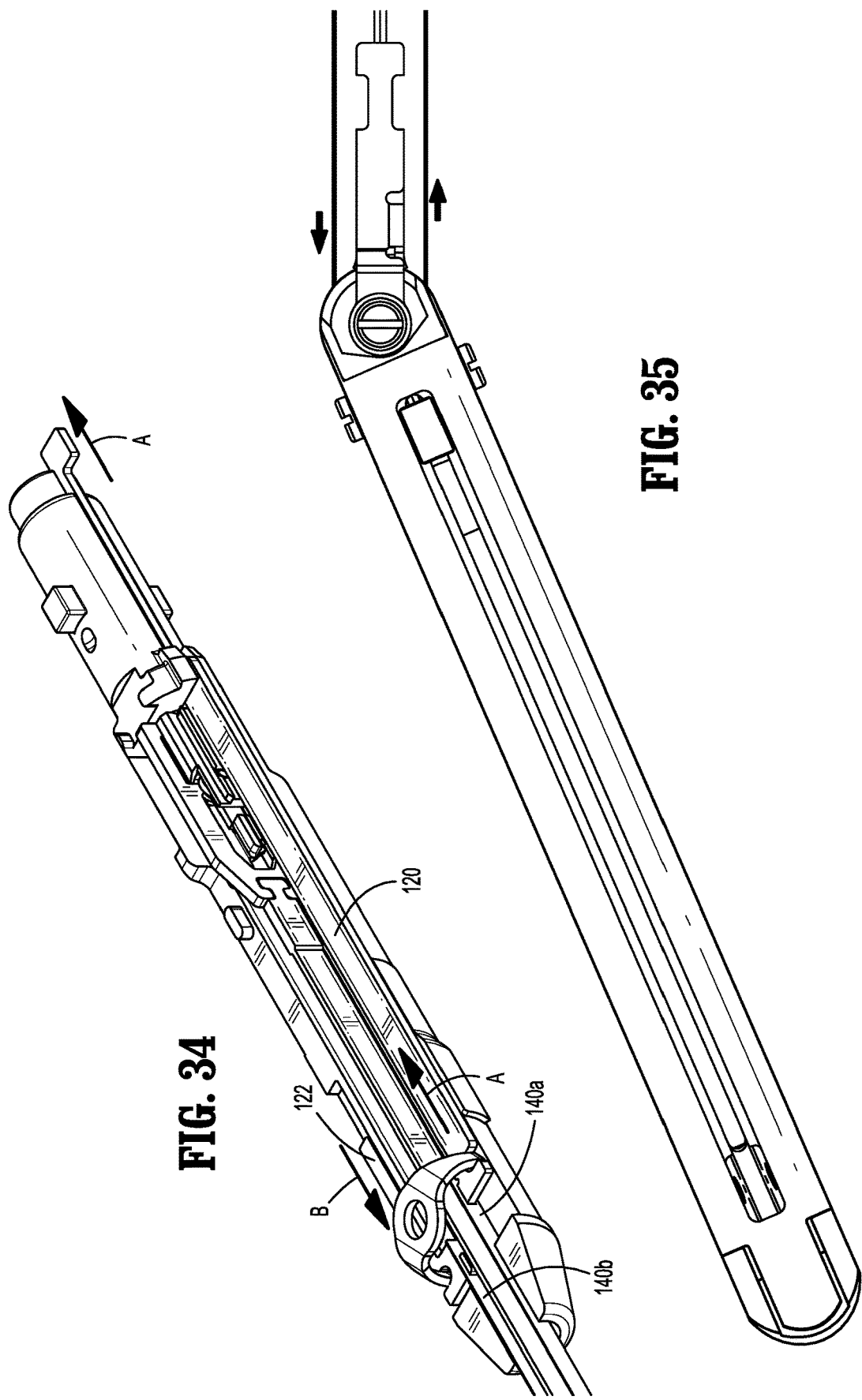

ENDOSCOPIC STAPLER AND STAPLE

CROSS-REFERENCE TO RELATED APPLICATIONS

This application is a divisional of U.S. patent application Ser. No. 14/803,249, filed Jul. 20, 2015, the disclosure of which is incorporated by reference herein in its entirety.

TECHNICAL FIELD

The present disclosure relates to surgical staplers, and more particularly, to surgical staplers for endoscopic use. The present disclosure also relates to surgical staples for use with endoscopic surgical staplers.

BACKGROUND

Surgical staplers typically include a cartridge housing a plurality of staples, an anvil for forming the staples as the staples are ejected from the cartridge and a knife to effect simultaneous dissection and suturing of tissue. When compared to applying manually threaded sutures, the use of surgical staplers to suture and dissect tissue has increased the speed of the surgical procedure and thus, minimized patient trauma.

In an endoscopic surgical procedure, a surgical stapler is inserted through a small incision in the skin or through a cannula to access a surgical site within a patent. Typically, staples are driven from a cartridge of the surgical stapler in a direction perpendicular to a tissue contact surface of the cartridge. Due to the complexity of known surgical staplers as well as the staple size requirements of known staple forming apparatus, a continued need exists for small diameter surgical staplers suitable for endoscopic use.

SUMMARY

The present disclosure is directed to a surgical stapler having a tool assembly including an anvil and a staple cartridge having a series of staples which are supported and configured to be rotatably ejected from the staple cartridge into the anvil to suture tissue. The manner in which the staples are supported and ejected from within the staple cartridge facilitates the use of a small diameter tool assembly that includes staples capable of suturing thicker tissues than would normally be associated with tool assemblies with such a small diameter.

In embodiments, the surgical stapler includes a cartridge that supports a plurality of rotatable pushers. Each pusher supports a curved, substantially U-shaped staple having a single tissue penetrating distal leg portion and a proximal leg portion. The pusher is rotatable to drive the distal leg portion into an anvil to deform the staple into a substantially D-shaped configuration.

In one aspect of the disclosure, a surgical stapler includes a shaft portion, and a tool assembly supported on a distal end of the shaft portion. The tool assembly includes an anvil and a cartridge assembly. The cartridge assembly includes a cartridge body defining a plurality of staple pockets, a pusher rotatably supported in each of the staple pockets, and a staple supported on each of the pushers. A drive assembly has a working member that is configured to move through the tool assembly to effect rotatable movement of each of the pushers within a respective one of the staple pockets, wherein rotatable movement of each of the pushers ejects the staple from the respective staple pocket of the cartridge body.

In embodiments, each of the staple pockets includes a pivot member and each of the pushers is rotatably supported on a respective one of the pivot members.

In some embodiments, each of the staple pockets includes a circular wall and each of the circular walls slidably supports a respective one of the pushers.

In certain embodiments, the cartridge body defines at least two rows of staple pockets and at least one channel that extends between the at least two rows of staple pockets.

In embodiments, the surgical stapler includes a sled configured to translate through the at least one channel. The sled includes at least one cam that is positioned to sequentially engage the pushers to effect rotatable movement of the pushers within the cartridge body.

In some embodiments, the sled is positioned within the cartridge body to be engaged and advanced by the working member of the drive assembly.

In certain embodiments, each of the pushers is positioned to extend into the at least one channel of the cartridge body such that translation of the sled through the at least one channel causes the at least one cam to contact the pushers in two adjacent rows of the at least two rows of staple pockets to effect rotation of the pushers.

In embodiments, the at least two rows of staple pockets includes four rows of staple pockets and the at least one cam includes two cams.

In some embodiments, each of the staples includes a single tissue penetrating leg portion.

In certain embodiments, the single tissue penetrating leg portion has a first end defining a tapered tip and a second end connected to a proximal leg portion. The proximal leg portion is supported on one of the pushers.

In embodiments, each of the pushers includes a body defining a channel and the proximal leg portion of each of the staples is supported within the channel.

In some embodiments, the single tissue penetrating leg portion is curved and is configured to slide along the circular wall of the staple pocket.

In certain embodiments, the cartridge assembly includes a cartridge channel that supports the cartridge body and the surgical stapler further includes first and second articulation links. Each of the first and second articulation links has a distal end operatively connected to a proximal end of the cartridge channel. The first and second articulation links are axially movable in opposite directions to pivot the tool assembly in relation to the shaft portion.

In embodiments, the surgical stapler further includes a pivotable articulation member interconnecting the first articulation link with the second articulation link, wherein pivotable movement of the articulation member causes movement of the first articulation link in one direction and effects movement of the second articulation link in an opposite direction.

In some embodiments, each of the pushers defines a slot dimensioned to receive the pivot member such that the pusher is to rotatably supported within a respective one of the plurality of staple pockets.

In certain embodiments, the blunt proximal leg portion of each of the staples includes a curved portion and the channel includes a bump. The bump interacts with the curved portion to retain the staple within a respective one of the plurality of staple pockets.

In embodiments, the working member of the drive assembly has a I-beam configuration including an upper beam and a lower beam. The upper and lower beams are engageable with the anvil and the cartridge assembly to progressively clamp tissue as the working member moves through the tool assembly.

In another aspect of the disclosure, a surgical staple includes a distal tissue penetrating leg portion including a first end having a tapered tip, a curved body, and a second end, and a proximal leg portion connected to the second end of the tissue penetrating leg portion. The proximal leg portion is configured to be received on a pusher, wherein the distal tissue penetrating leg portion and the proximal leg portion are configured to have a D-shaped deformed configuration.

In another aspect of the disclosure, a tool assembly includes an anvil and a cartridge assembly. The cartridge assembly has a cartridge body defining a plurality of staple pockets, a pusher rotatably supported in each of the staple pockets, and a staple supported on each of the pushers.

In embodiments, each of the staple pockets includes a pivot member and each of the pushers is rotatably supported on a respective one of the pivot members.

In some embodiments, each of the staple pockets includes a circular wall that slidably supports a respective one of the pushers.

In certain embodiments, the cartridge body defines at least two rows of staple pockets and at least one channel that extends between the at least two rows of staple pockets.

In embodiments, the surgical stapler further includes a sled configured to translate through the at least one channel. The sled includes at least one cam that is positioned to sequentially engage the pushers to effect rotatable movement of the pushers within the cartridge body.

BRIEF DESCRIPTION OF THE DRAWINGS

Various embodiments of the presently disclosed surgical stapler and surgical staple are described herein with reference to the drawings, wherein:

FIG. 1A is a side perspective view from the distal end of a stapler reload of the surgical stapler shown in FIG. 1;

FIG. 7 is a top view of the cartridge body of the cartridge assembly of the surgical stapler reload shown in FIG. 1A;

FIG. 8 is a bottom view of the cartridge body, pushers and sled of the cartridge assembly of the surgical stapler reload shown in FIG. 1A;

FIG. 9 is a cross-sectional view taken along section line 9-9 of FIG. 7;

FIG. 10 is a cross-sectional view taken along section line 10-10 of FIG. 7;

FIG. 15 is a side cross-sectional view taken along section line 15-15 of FIG. 4;

FIG. 16 is an enlarged view of the indicated area of detail shown in FIG. 15;

FIG. 21 a cross-sectional view taken along section line 21-21 of FIG. 17;

FIG. 22 is an enlarged view of the indicated area of detail shown in FIG. 21;

FIG. 25 is a cross-sectional view through the tool assembly shown in FIG. 24;

FIG. 26 is an enlarged view of the indicated area of detail shown in FIG. 25;

FIG. 27 is a side cross-sectional view of the tool assembly of the stapler reload of the surgical stapler shown in FIG. 1 with the tool assembly in the approximated position and drive member partially advanced to fire staples from the cartridge assembly;

FIG. 28 is an enlarged view of the indicated area of detail shown in FIG. 27;

FIG. 32 is a top perspective view of the proximal body portion of the stapler reload shown in FIG. 31 with the proximal tube and the upper housing half section removed;

FIG. 33 is a top perspective view of the upper housing half-section of the proximal body portion of the stapler reload shown in FIG. 31;

FIG. 34 is a top, perspective view of the proximal body portion of the stapler reload shown in FIG. 33 with the proximal tube and the upper housing half section removed and the articulation member rotated; and FIG. 35 is a top view of the tool assembly of the stapler reload shown in FIG. 31 in an articulated position.

DETAILED DESCRIPTION OF EMBODIMENTS

Figure 1:
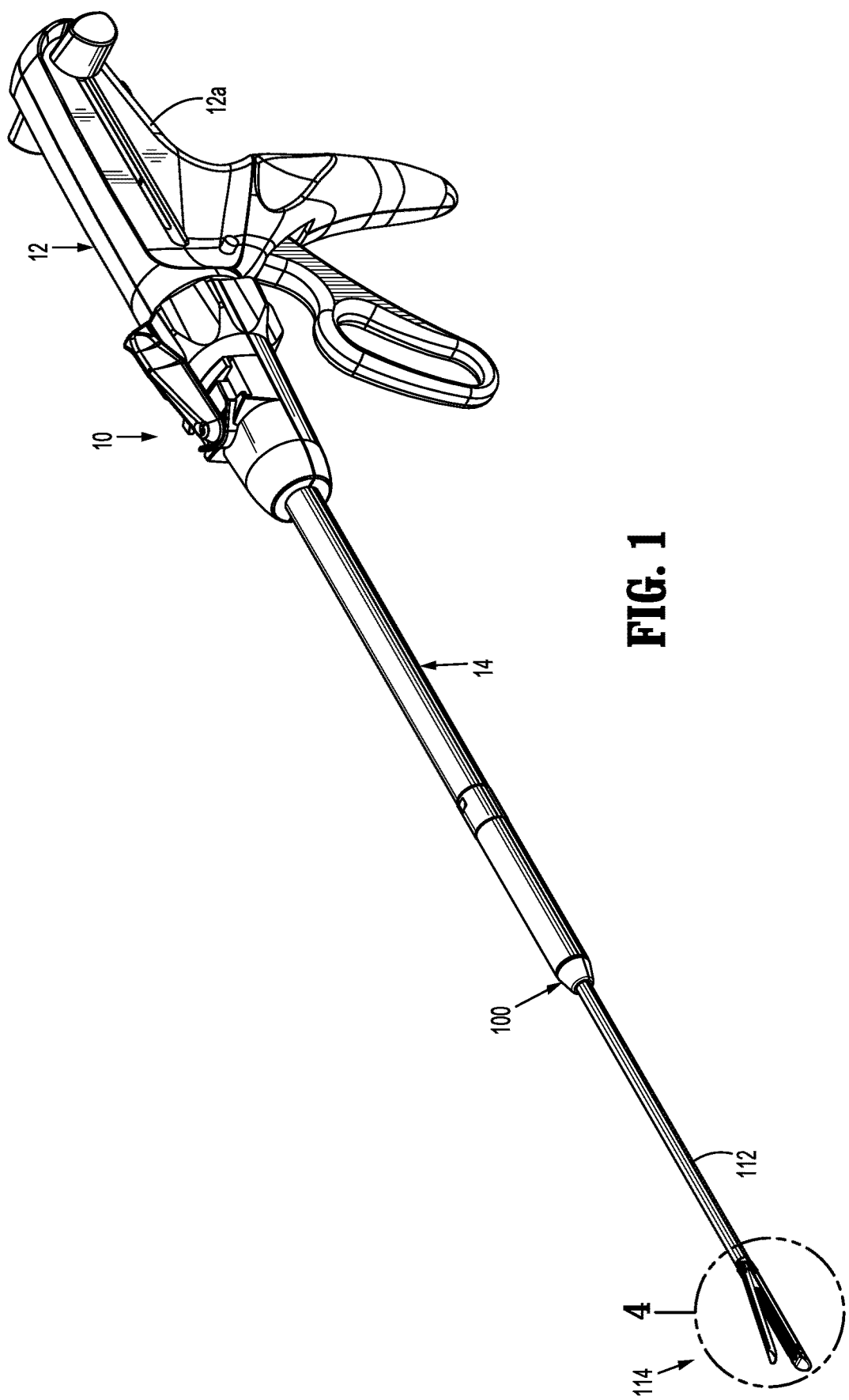
FIG. 1 is a side perspective view of one embodiment of the presently disclosed surgical stapler in an unapproximated position.

Embodiments of the presently disclosed endoscopic surgical stapler including staples for endoscopic use will now be described in detail with reference to the drawings wherein like reference numerals designate identical or corresponding elements in each of the several views. In this description, the term "proximal" is used generally to refer to the portion of the apparatus that is closer to a clinician, while the term "distal" is used generally to refer to the portion of the apparatus that is farther from the clinician. In addition, the term "endoscopic" is used generally to refer to endoscopic, laparoscopic, or arthroscopic apparatus or procedures as well as any other surgical apparatus or procedure that is configured to extend or be performed through a small incision or a cannula inserted into a patient's body. Finally, the term "clinician" is used generally to refer to medical personnel including doctors, nurses, and support personnel.

The presently disclosed surgical stapler includes a tool assembly which supports a plurality of staples which are supported and configured to be rotatably ejected from a staple cartridge into an anvil to suture tissue. The manner in which the staples are supported and ejected from within the staple cartridge facilitates the use of a small diameter tool assembly which includes staples capable of suturing thicker tissues than would normally be associated with tool assemblies with such a small diameter. In embodiments, the surgical stapler includes a cartridge that supports a plurality of rotatable pushers. Each pusher supports a substantially U-shaped staple having a single tissue penetrating distal leg portion and a proximal leg portion. The distal leg portion is positioned on the pusher to be driven into an anvil to deform the U-shaped staple into a substantially D-shape.

Figure 2:
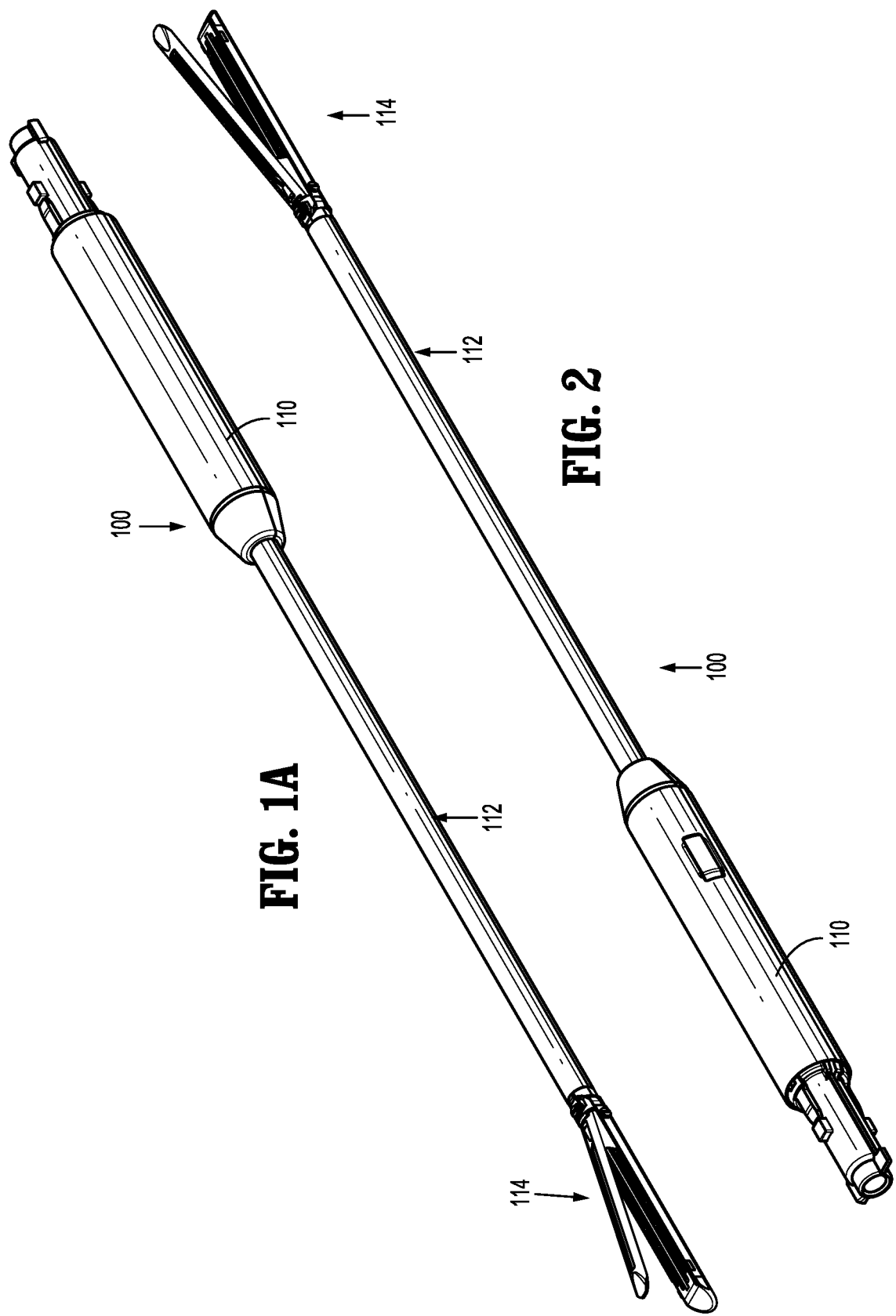
FIG. 2 is a side perspective view from the proximal end of the surgical stapler reload shown in FIG. 1A.

FIG. 1-2 illustrate the presently disclosed surgical stapler 10 which includes an actuating device 12 having a handle assembly 12a, a body portion 14 that extends distally from the handle portion 12a, and a stapler reload 100 supported on a distal end of the body portion 14. The distal end of the body portion 14 is adapted to releasably engage a proximal end of the reload 100 such that actuation of the actuating device 12 effects operation of the reload 100. Suitable actuating devices are disclosed in detail in U.S. Pat. No. 5,865,361 ("361 patent") and U.S. Pat. No. 7,143,924 ("924 patent") which are incorporated herein in their entirety by reference. Although the presently disclosed actuating device is illustrated as a manually actuated handle assembly, it is envisioned that other known actuating devices including robotic devices, motorized devices, and/or electrically or mechanically driven devices can be used to actuate the reload 100.

In alternate embodiments, the reload 100 can be fixedly attached to the distal end of the handle assembly 12. In such embodiments, a cartridge assembly of a tool assembly may be removable to facilitate reuse of the surgical stapler 10.

Referring to FIGS. 1A-3, the reload 100 includes a proximal body portion 110, an elongated shaft portion 112 and a tool assembly 114. The proximal body portion 110 includes an inner housing 116 (FIG. 23) including an upper housing half-section 116a and a lower housing half-section 116b. The housing half-sections 116a and 116b define channels which slidably receive a proximal drive member 118, a first articulation link 120 and a second articulation link 122. The first articulation link 120 is connected to the second articulation link 122 by an articulation member 123 which will be described in detail below. The housing half-sections 116a and 116b are received within a proximal body tube 125.

Figure 3:
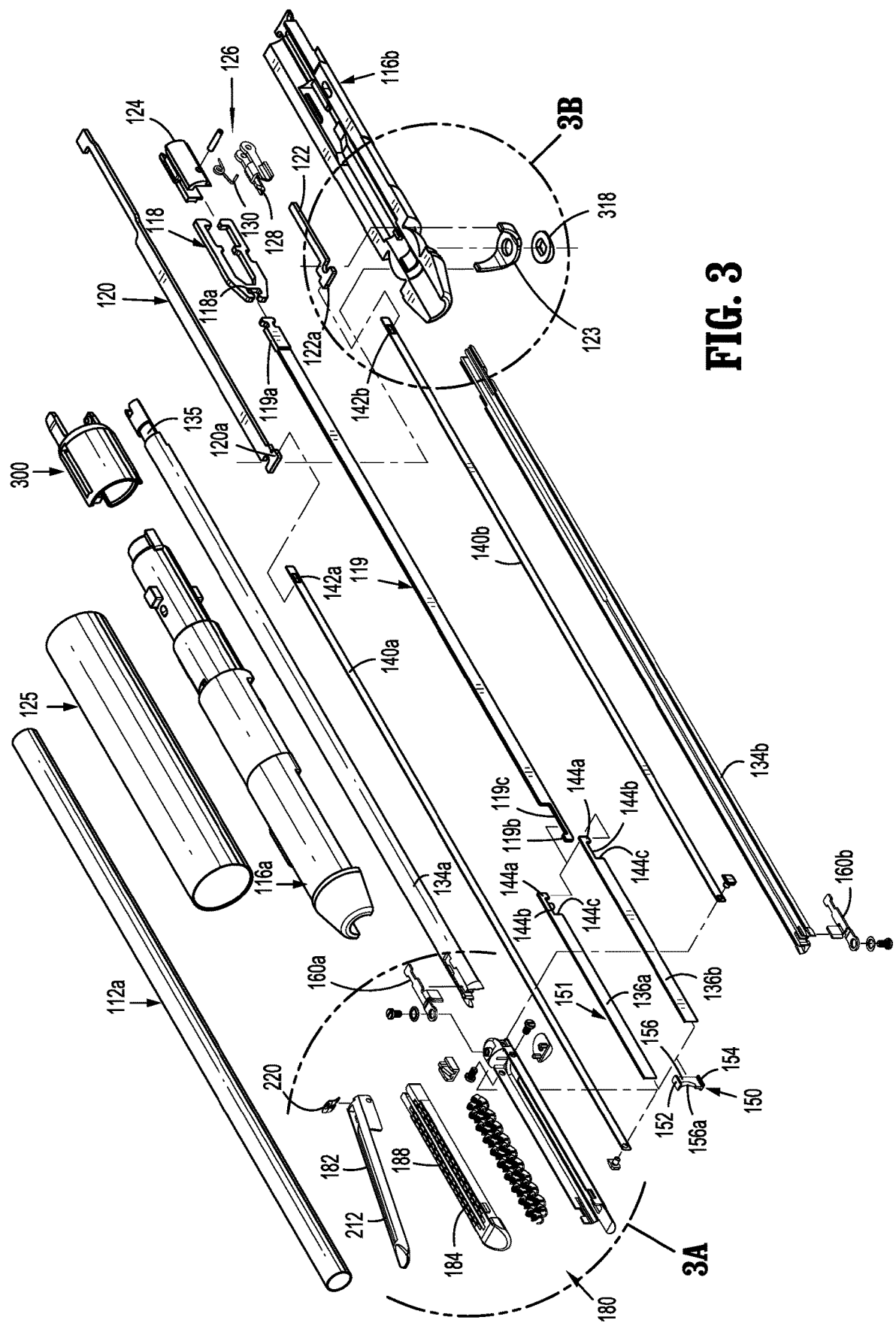
FIG. 3 is a side perspective, exploded view of the surgical stapler reload shown in FIG. 1A.
Figure 3A:
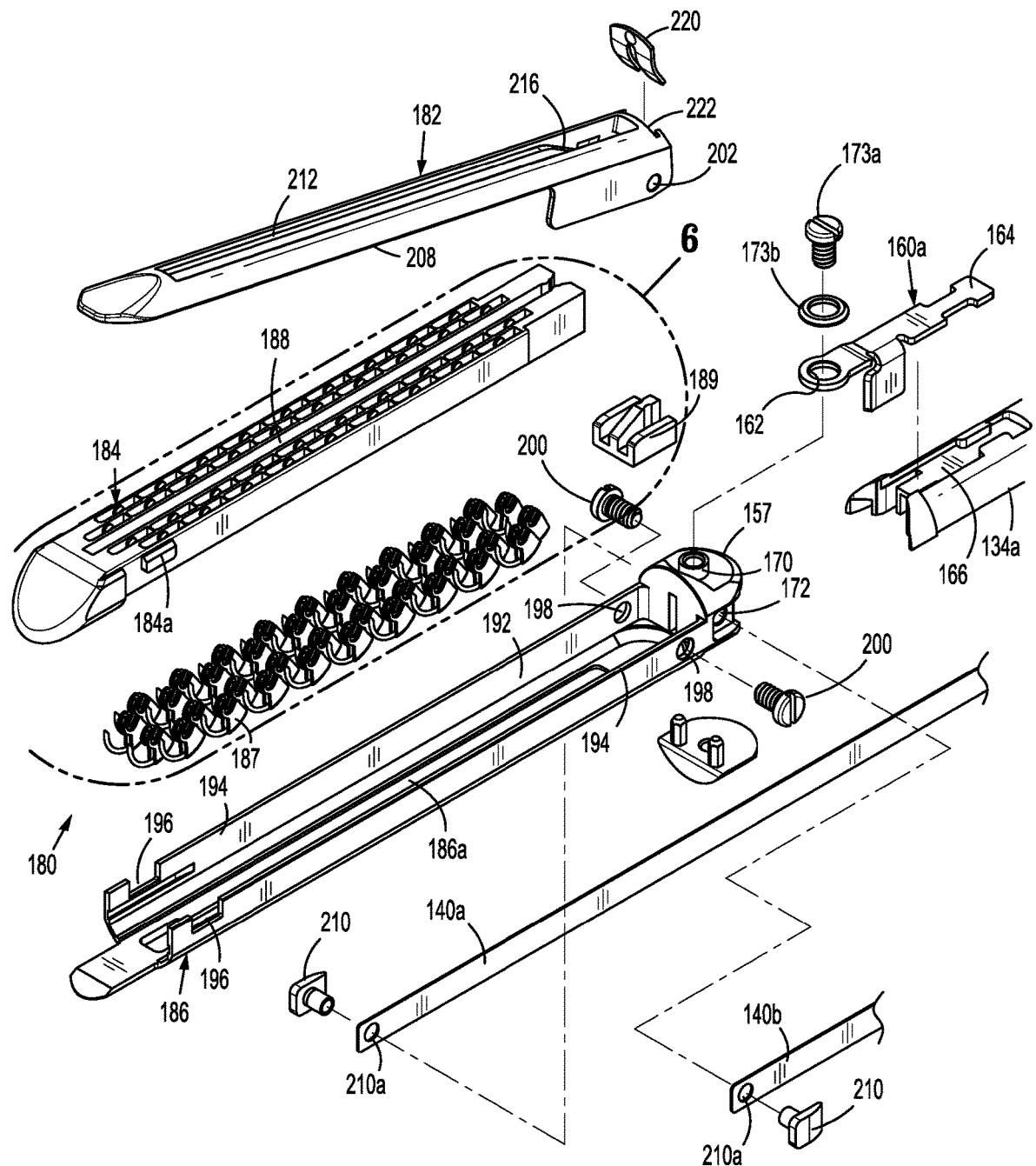
FIG. 3A is an enlarged view of the indicated area of detail shown in 3.
Figure 3B:
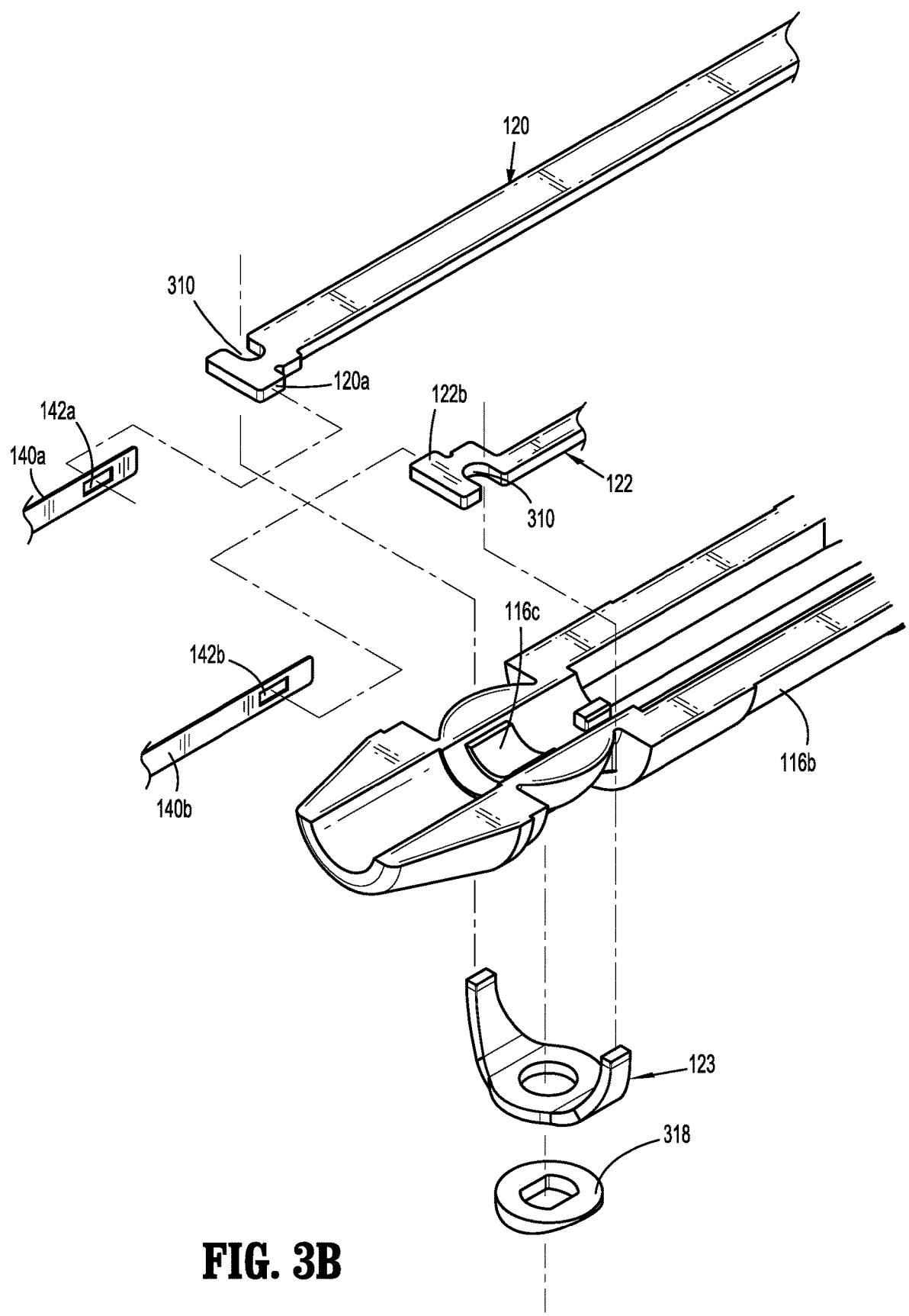
FIG. 3B is an enlarged view of the indicated area of detail shown in FIG. 3.

Referring to FIGS. 3-3B, the proximal drive member 118 supports a drive coupler 124 that is adapted to engage a control rod (not shown) of the actuating device 12 (FIG. 1) to operate the tool assembly 114 of the reload 100. The proximal drive member 118 also supports a locking assembly 126 which includes a locking device 128 and a spring 130. Operation of the drive coupler 124 and the locking assembly 126 are described in the '361 patent. Accordingly, the drive coupler 124 and locking assembly 126 will not be described in further detail herein. A distal end of the proximal drive member 118 includes a T-shaped recess 118a. In addition, the distal ends of the first articulation link 120 and the second articulation link 122 include hook portions 120a and 122a, respectively (FIG. 3B). Each of these hook portions 120a and 122a and the T-shaped recess 118a are described in further detail below.

Figure 18:
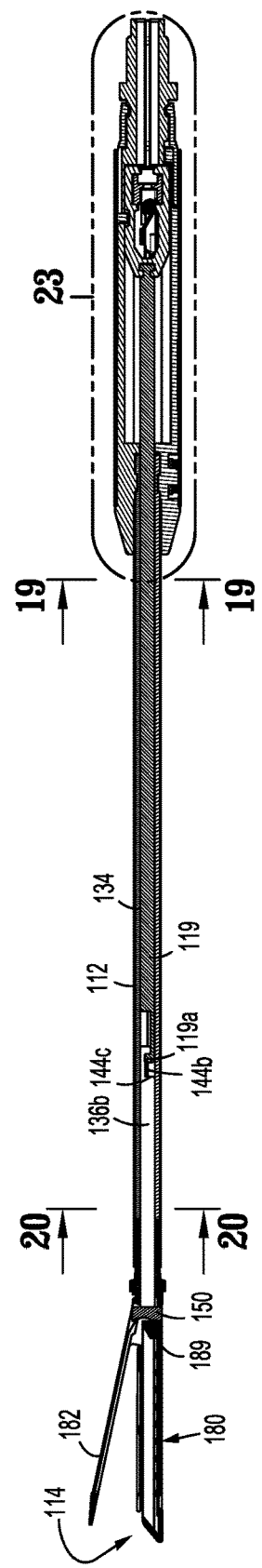
FIG. 18 is a side cross-sectional view taken along section line 18-18 of FIG. 17.
Figure 19:
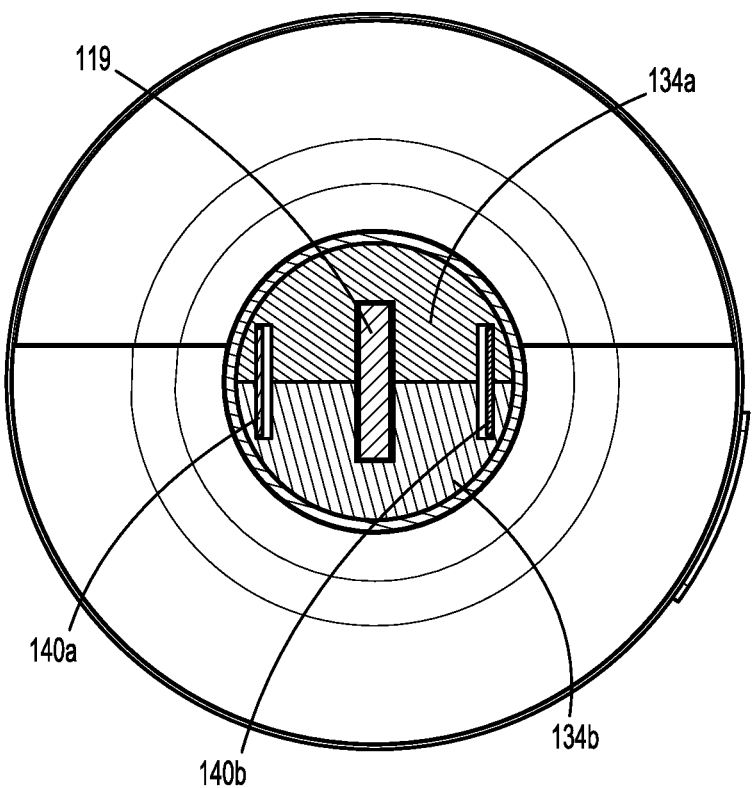
FIG. 19 is a cross-sectional view taken along section line 19-19 of FIG. 18.
Figure 20:
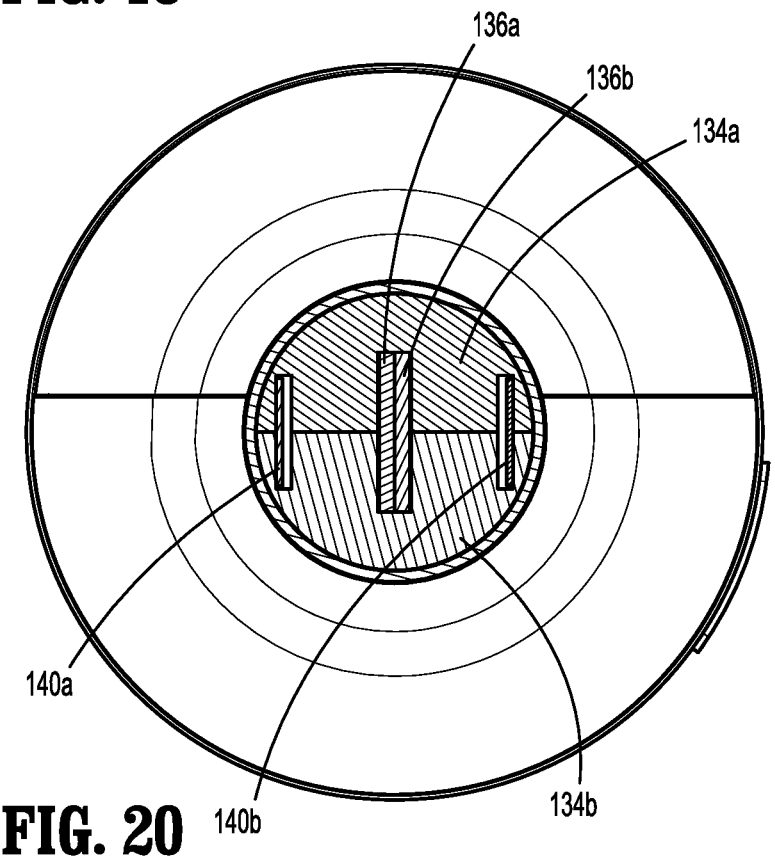
FIG. 20 a cross-sectional view taken along section line 20-20 of FIG. 18.
Figure 23:
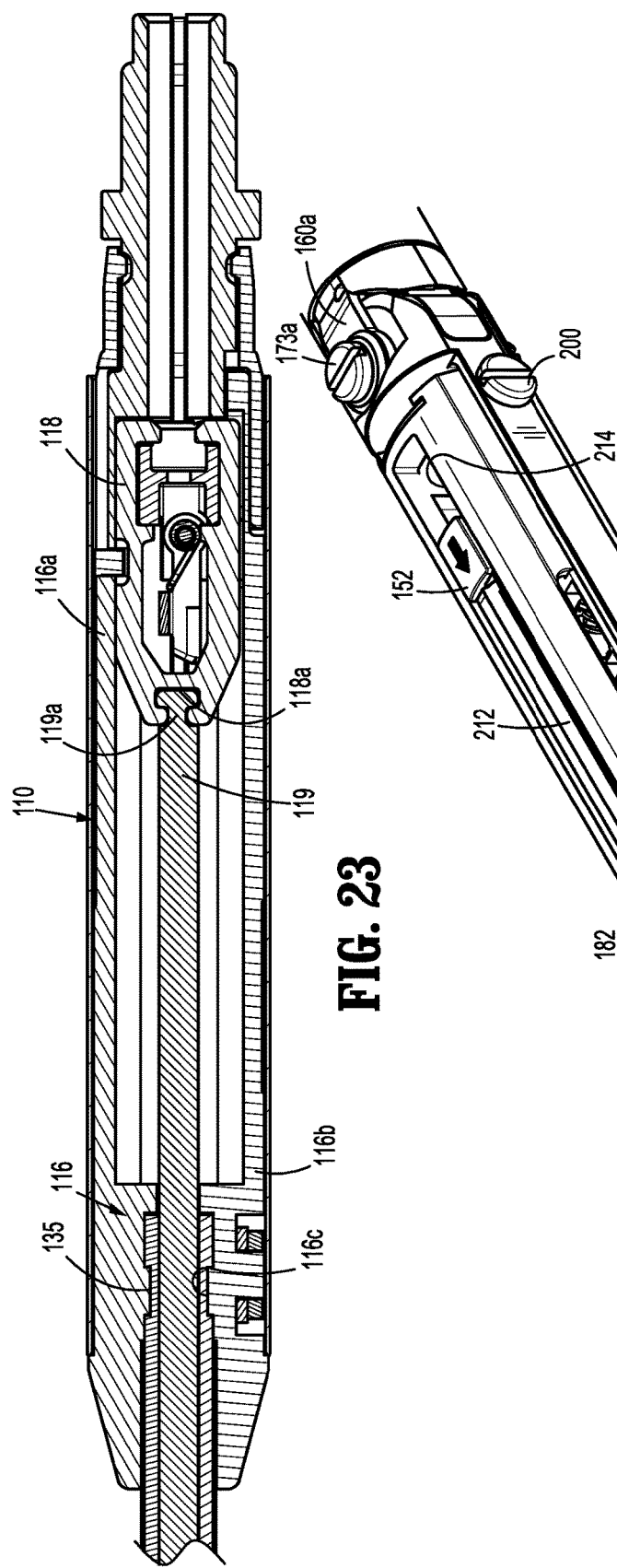
FIG. 23 is an enlarged view of the indicated area of detail shown in FIG. 18.

The elongated shaft portion 112 of the reload 100 includes an inner housing 134 (FIG. 18) including upper and lower housing half-sections 134a and 134b which are received within a shaft portion tube 112a. A proximal end of the inner housing 134 of the elongated shaft portion 112 is received within the distal end of the inner housing 116 of the proximal body portion 110 and includes an annular recess 135 (FIG. 23). The annular recess 135 receives a protrusion 116c formed within the inner housing 116 to axially secure the inner housing 116 of the proximal body portion 110 to the inner housing 134 of the shaft portion 112. The upper and lower housing half-sections 134a, 134b of the elongated shaft portion 112 define internal channels (not shown) which slidably receive a pair of distal drive members 136a, 136b and a pair of articulation rods 140a, 140b. A proximal end of each of the articulation rods 140a, 140b defines a cutout 142a, 142b, respectively. The cutouts 142a, 142b of the articulation rods 140a, 140b receive one side of the hook portions 120a, 122a, (FIG. 3B), respectively, of the first and second articulation links 120, 122. When the hook portions 120a, 122a are received within the cutouts 142a, 142b of the articulation rods 140c, 140b, linear movement of the first and second articulation links 120, 122 effects linear movement of the articulation rods 140a, 140b as described in further detail below.

A proximal end of each of the distal drive members 136a, 136b includes a hook portion 144a and defines a recess 144b. Each of the recesses 144b is defined by a distal wall 144c. The proximal drive member 118 and the proximal end of the distal drive members 136a, 136b are connected by a drive member link 119. The drive member link 119 has a proximal end 119a (FIG. 23) configured to be received in the T-shaped slot 118a of the proximal drive member 118. A distal end of the drive member link 119 includes a hook portion 119b and defines a recess 119c. The hook portion 119b is received within the recesses 144b of the distal drive members 136a, 136b such that the hook portions 144a of the distal drive members 136a, 136b are slidably received within the recess 119c of the drive member link 119. Movement of the proximal drive member 118 effects corresponding movement of the drive member link 119. As the drive member link 119 is moved distally, the hook portion 119b of the drive member link 119 moves within the recesses 144b of the distal drive members 136a, 136b such that the drive member link 119 moves independently of the drive members 136a, 136b. When the hook member 119a of the drive member link 119 engages the distal walls 144c defining the recesses 144b of the distal drive members 136a, 136*b*, distal movement of the drive member link 119 will effect corresponding distal movement of the distal drive members 136*a*, 136*b*. By controlling the length the recesses 144*b*, the length of movement or the stroke of the drive members 136*a*, 136*b* can be controlled to facilitate use of the components of the proximal body portion 110 of the reload 100 with different length tool assemblies 114. It is envisioned that the proximal drive member 118, the drive member link 119, and/or the distal drive members 136*a*, 136*b* can be formed as a unitary component.

Figure 4:
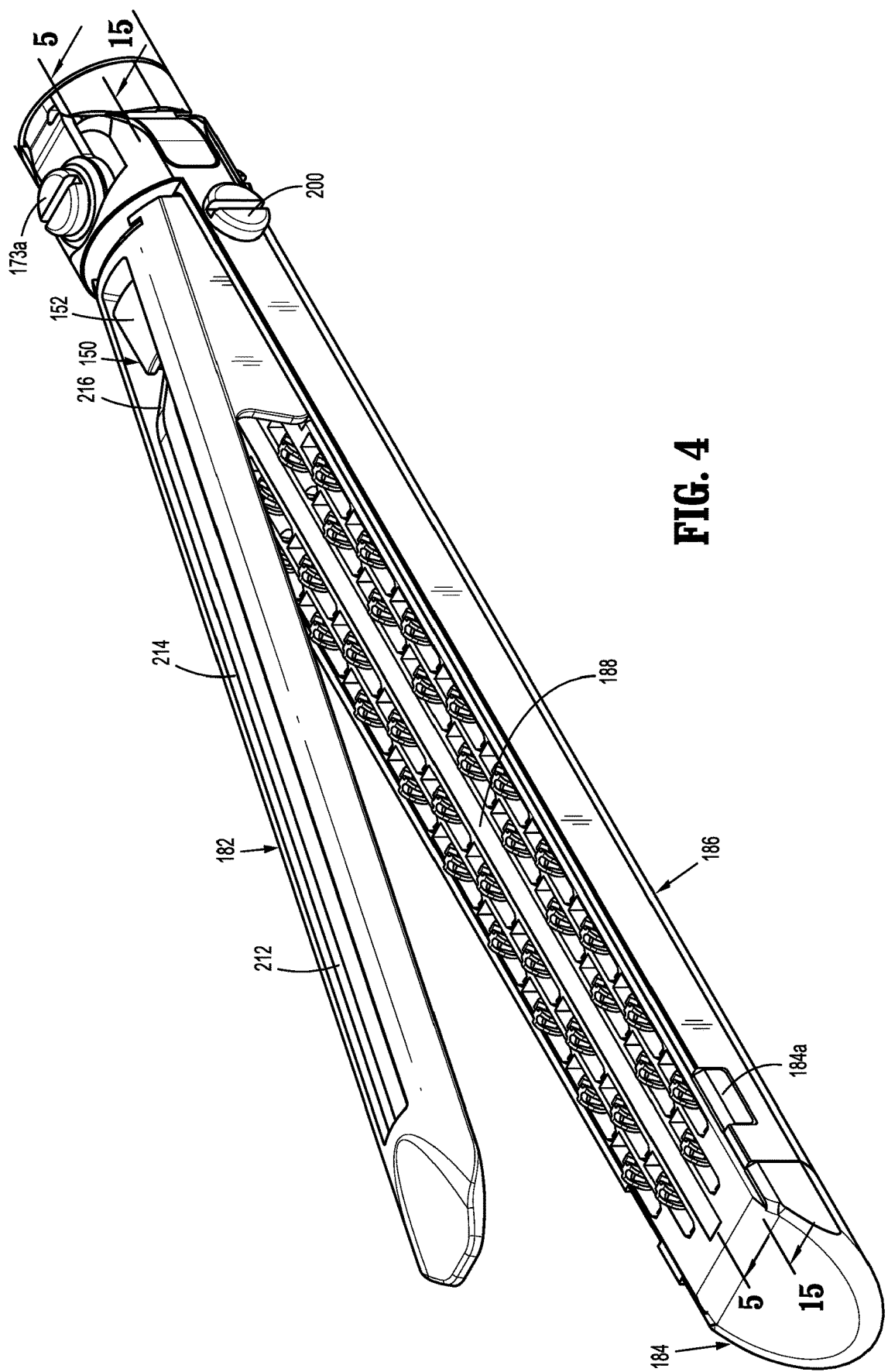
FIG. 4 is an enlarged view of the indicated area of detail shown in FIG. 1.
Figure 5:
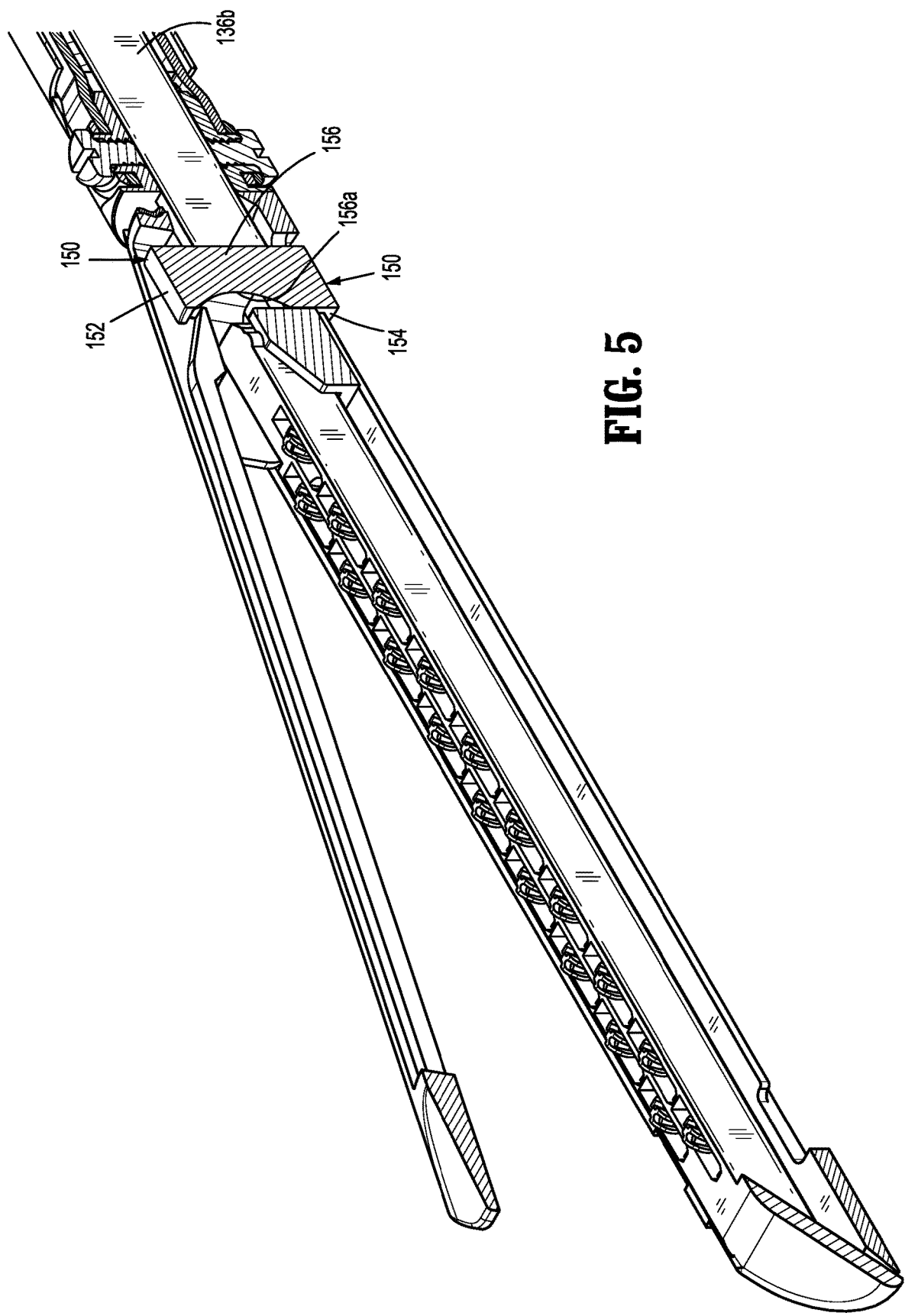
FIG. 5 is a cross-sectional taken along section line 5-5 of FIG. 4.

Referring to FIGS. 3-5, the distal end of each of the distal drive members 136*a* and 136*b* is secured to a working member 150 (FIG. 5) such as by welding to form a drive assembly 151. Alternately, other securement techniques can be used to secure the distal end of the drive members 136*a*, 136*b* to the working member 150. In one embodiment, the working member 150 includes an upper beam 152, a lower beam 154 and a vertical strut 156 interconnecting the upper and lower beams 152, 154. A cutting edge 156*a* is formed or supported on a distal end of the vertical strut 156. The vertical strut 156 is configured to translate through the tool assembly 114 when the tool assembly 114 is actuated by the actuating device 12 to fire the staples and dissect tissue. More specifically, the vertical strut 156 is positioned to translate through a knife slot 188 formed in a cartridge body 184 of a cartridge assembly 180 and a slot 212 formed in the anvil 182 to dissect tissue clamped between the anvil 180 and the cartridge body 184 and eject staples from the cartridge body 184 as will be described in further detail below.

Referring again to FIGS. 3 and 3A, the cartridge body 184 is supported within a cartridge channel 186 (FIG. 3A) of the cartridge assembly 180. The cartridge channel 186 includes a pivot member 157 that is secured to a distal end of the shaft housing half-sections 134*a*, 134*b* by upper and lower connecting members 160*a*, 160*b*. Each connecting member 160*a*, 160*b* includes a distal end which defines an opening 162 and a proximal end 164 which has a stepped configuration. The stepped configuration of the proximal end 164 of each connecting member 160*a*, 160*b* is received within a cutout 166 formed in the distal end of each of the upper and lower shaft housing half-sections 134*a*, 134*b* to axially fix the upper and lower connecting members 160*a*, 160*b* to the upper and lower shaft housing half-sections 134*a*, 134*b*, respectively. The openings 162 of each of the upper and lower connecting members 160*a*, 160*b* receive a respective pivot pin 170 (only one shown, FIG. 3A) formed on the upper and lower surfaces of the pivot member 157 to pivotally secure the pivot member 157, and thus, the cartridge channel 186, to the shaft housing half-sections 134*a*, 134*b*. A screw 173*a* and a washer 173*b* are provided to secure each of the connecting members 160*a*, 160*b* to the pivot member 157. The pivot member 157 also includes two transversely extending bores 172. Each of the bores 172 receives a pin 210 that also passes through an opening 210*a* (FIG. 3A) in a distal end of the articulation rods 140*a*, 140*b* to secure the pivot member 157 between the distal ends of the articulation rods 140*a*, 140*b*. As discussed in further detail below, when the articulation rods 140*a*, 140*b* are translated in opposite directions, the cartridge channel 186 is pivoted about an axis defined by the pivot pins 170 to pivot the tool assembly 114 in relation to the elongated shaft portion 112 of the reload 100.

Referring to FIGS. 3-6, the cartridge assembly 180 (FIG. 6) includes the cartridge body 184, the cartridge channel 186, a plurality of pushers 187, a sled 189, and a plurality of staples 190. The cartridge body 184 includes a tapered distal end 184*a* that functions as a tissue guide to direct tissue between the anvil 182 and the cartridge body 184. The cartridge channel 186 defines a recess 192 (FIG. 3A) that receives the cartridge body 184 and an elongated slot 186*a* that is aligned with the knife slot 188 formed in the cartridge body 184. The recess 192 is defined in part by sidewalls 194 of the cartridge channel 186. In embodiments, each of the sidewalls 194 defines a cutout 196 that receives protrusions 184*a* formed on the outer surface of the cartridge body 184 to secure the cartridge body 184 within the recess 192 of the cartridge channel 186. It is envisioned that other techniques may be used to secure the cartridge body 184 within the cartridge channel 186.

In embodiments, the sidewalls 194 of the cartridge channel 186 defines openings 198 that receive pivot members 200 (FIG. 3A). The pivot members 200 extend through openings 202 defined in the proximal end of the anvil 182 and into the openings 198 in the cartridge channel 186 to pivotally secure the anvil 182 to the cartridge channel 186.

The anvil 182 includes a tissue engaging surface 208 that defines a plurality of anvil pockets 210 (FIG. 28) that receive the staples 190. As discussed above, the anvil 182 defines an elongated slot 212 that receives the vertical strut 156 of the working member 150 of the drive assembly 151. The anvil 182 also defines an elongated recess 214 that slidably receives the upper beam 152 of the working member 150. The elongated recess 214 defines a proximal cam surface 216. When the upper beam 152 engages the proximal cam surface 216 as the working member 150 is translated distally through the elongated recess 214 of the anvil 182, the upper beam 152 of the working member 150 urges the anvil 182 towards the cartridge body 184 to move the tool assembly 114 to a clamped or approximated position. A biasing member, e.g., leaf spring 220, is supported in a slot 222 (FIG. 3A) defined between the proximal end of the anvil 182 and the distal end of the pivot member 157 of the cartridge channel 186 to urge the anvil 182 away from the cartridge body 184 to an open or unclamped position.

Figure 6:
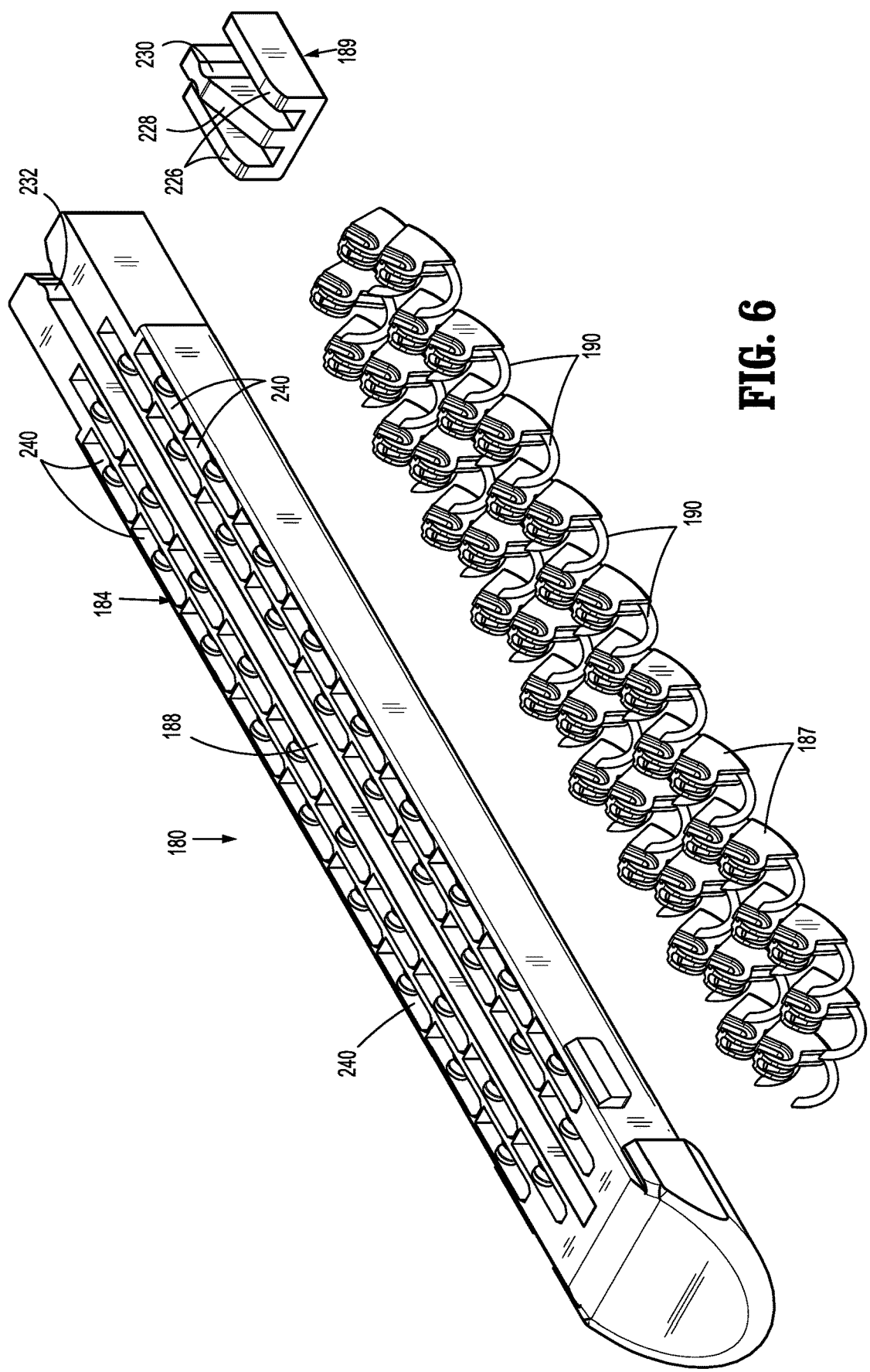
FIG. 6 is an enlarged view of the indicated area of detail shown in FIG. 3A.
Figure 11:
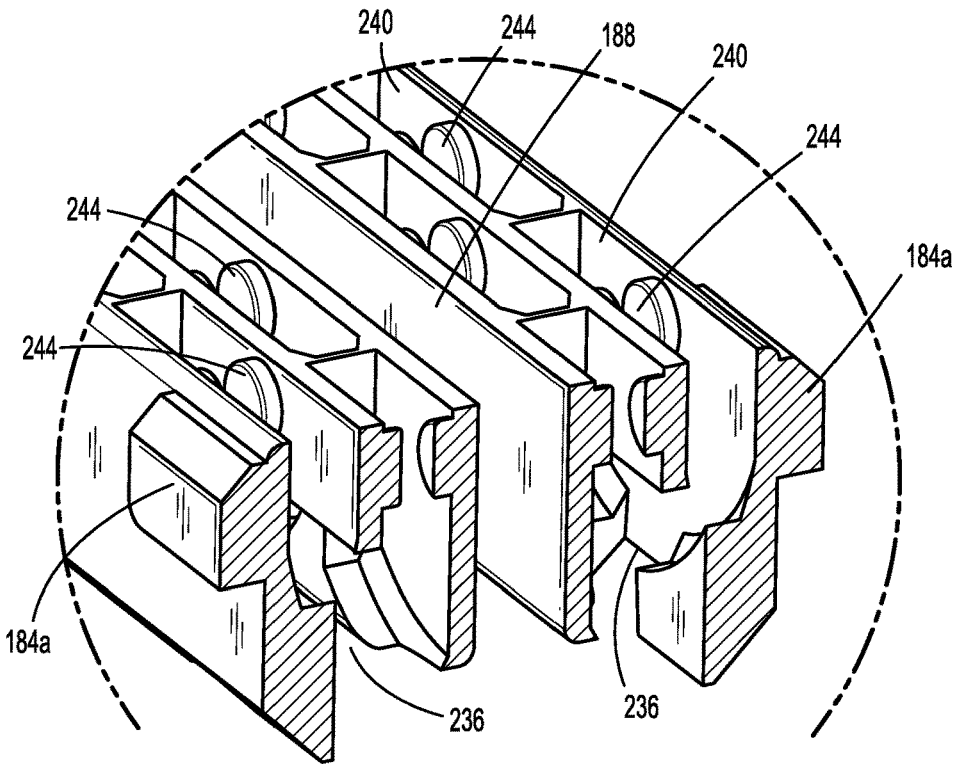
FIG. 11 is an enlarged view of the indicated area shown in FIG. 10.
Figure 12:
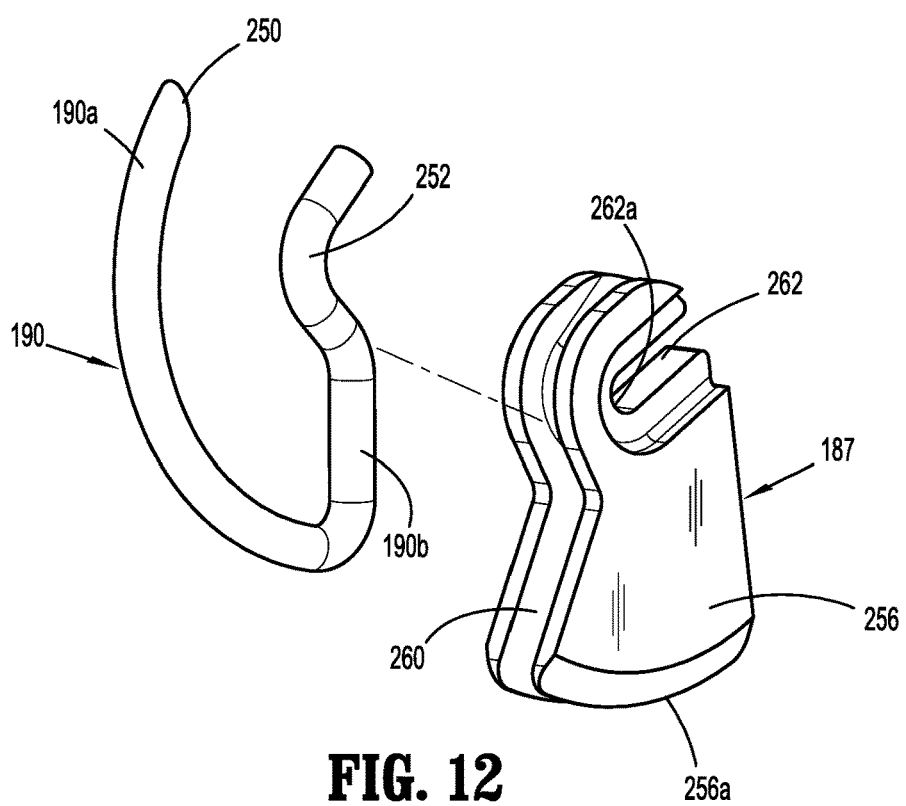
FIG. 12 is a side perspective view with parts separated of the staple and pusher of the cartridge assembly of the surgical stapler reload shown in FIG. 1A assembled.
Figure 13:
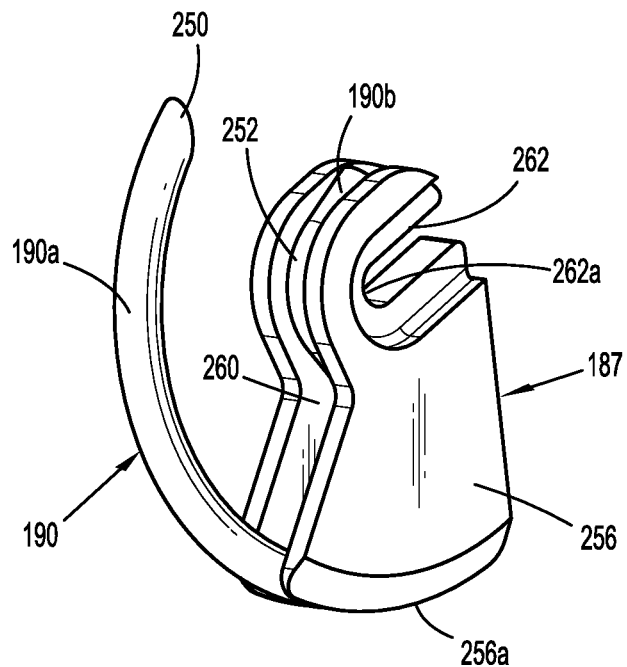
FIG. 13 is a side perspective view from the distal end of the staple and pusher of the cartridge assembly of the surgical stapler reload shown in FIG. 1A.
Figure 14:
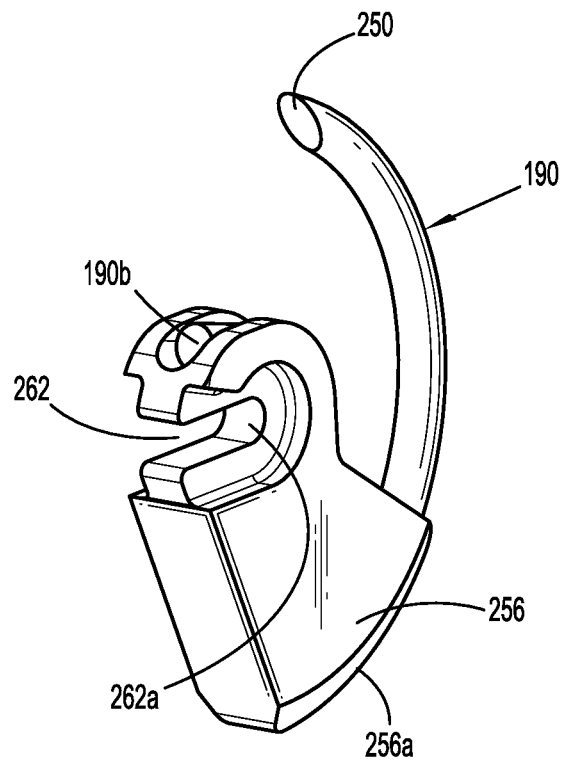
FIG. 14 is a side perspective view from the proximal end of a staple and a pusher of the cartridge assembly of the surgical stapler reload shown in FIG. 1A.
Figure 17:
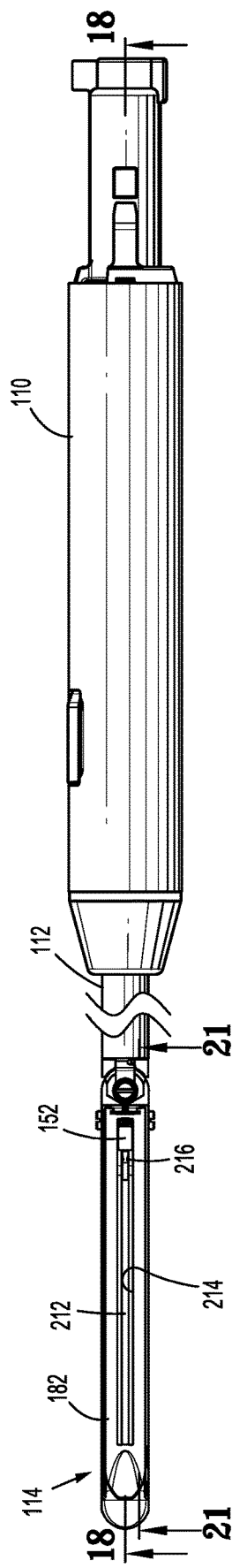
FIG. 17 is a top view of the surgical stapler reload shown in FIG. 1A.

Referring to FIG. 6, the sled 189 is positioned within the cartridge body 184 immediately distal of the working member 150 and includes cams 226 and a central rib 228. The cartridge body 184 defines channels 236. The sled 189 is configured to translate through the cartridge body 184 in response to translation of the working member 150 of the drive assembly 151 through the cartridge body 184 to effect translation of the central rib 228 through the knife slot 188 of the cartridge body 184 and translation of the cams 226 through the channels 236 of the cartridge body 184. The central rib 228 of the sled 189 defines detents 230 that receive protrusions 232 formed on the cartridge body 184 adjacent the proximal end of the knife slot 188 to releasably retain the sled 189 in a proximal position within the cartridge body 184. The cams 226 of the sled 189 are positioned to slide through channels 236 defined in the cartridge body 184 to engage the pushers 187 and eject the staples 190 from the cartridge body 184 as discussed in further detail below.

Referring also to FIGS. 7-11, the cartridge body 184 defines a plurality of staple pockets 240 which are positioned adjacent the channels 236 (FIG. 11) within the cartridge body 184. Each staple pocket 240 opens onto a tissue contacting surface 241 of the cartridge body 184 and includes a circular wall 242 and a pivot member 244. Each circular wall 242 supports a pusher 187 and the staple 190 such that each pusher 187 extends partially into a respective channel 236 of the cartridge body 184

Referring also to FIGS. 12-16, each staple 190 has a distal tissue penetrating leg portion 190*a* and a proximal blunt leg portion 190b. The distal leg portion 190a has a tapered tip 250 configured to penetrate tissue and a curved body configured to rest on the circular wall 242 of the staple pocket 240. The proximal leg portion 190b includes a recessed or curved portion 252 that is configured to retain the staple 190 in engagement with the pusher 187.

Each pusher 187 has a body 256 defining a channel 260 configured to receive the proximal leg portion 190b of one of the staples 190 and a slot 262 dimensioned to receive the pivot member 244 of the cartridge body 184. The channel 260 includes a curved portion or bump 260a that interacts with the curved portion 252 of the proximal blunt leg portion 190b to retain the staple 190 in the staple pocket 240. One end of the slot 262 includes a curved surface 262a that is configured to facilitate rotation of the pusher 187 about the pivot member 244 of the cartridge body 184 within the staple pocket 240. The body 256 of the pusher 187 also has a curved lower surface 256a that is positioned to slide along the circular wall 242 of the staple pocket 240 as the pusher 187 is rotated within the staple pocket 240. As discussed above, when each respective pusher 187 and staple 190 are supported within a staple pocket 240, each pusher 187 extends into a respective channel 236 of the cartridge body 184 in a position to engage one of the cams 226 of the sled 189 as the sled 189 translates through the cartridge body 184. When the sled 189 translates through cartridge body 184, the cams 226 of the sled 189 engage and rotate respective pushers 187 to sequentially eject the staples 190 from the cartridge body 184 as discussed in further detail below.

The slot 262 of the body 256 of each of the pushers 187 is positioned to receive the pivot members 244 to rotatably support each of the pushers 187 within a respective staple pocket 240. The slots 262 provide flexibility to the pushers 187 and help during assembly of the cartridge assembly 180 to overcome a small interference that holds each of the pushers 187 engaged with the pivot members 244 in the cartridge body 184.

Referring briefly again to FIG. 3, the reload 100 includes a locking member 300 which is rotatably supported about a proximal end of the inner housing 116 of the proximal body portion 110. The locking member 300 is movable from a first position in which the locking member 300 blocks distal movement of the proximal drive member 118 to a second position in which the locking member 300 moves to a position to allow distal movement of the proximal drive member 118. U.S. Pat. No. 7,143,924 describes the locking member 300 and its method of operation in detail and is incorporated herein by reference in its entirety.

Referring to FIGS. 17-23, when the proximal drive member 118 (FIG. 23) is in a retracted position, the drive member link 119 and, thus, the distal drive members 136a, 136b (FIG. 21) are also in a retracted position. In the retracted position, the hook portion 119a of the drive member link 119 is received within the recesses 144b of the distal drive members 136a, 136b (FIG. 3). In addition, the distal end of the upper beam 152 (FIG. 17) of the working member 150 is positioned proximally of the cam surface 216 (FIG. 18) of the anvil 182 to allow the spring 220 (FIG. 22) to move the anvil 182 to the unclamped or open position spaced from the cartridge body 184. As illustrated, the spring 220 is positioned in the slot 222 and presses against the proximal end of the anvil 182 to urge the anvil 182 towards the clamped position. As discussed above, the sled 189 is positioned immediately distal of the working end 150 of the drive assembly 151. Prior to advancement of the working member 150, the sled 189 is positioned proximally of the pushers 187 and staples 190 (FIG. 22).

Figure 24:
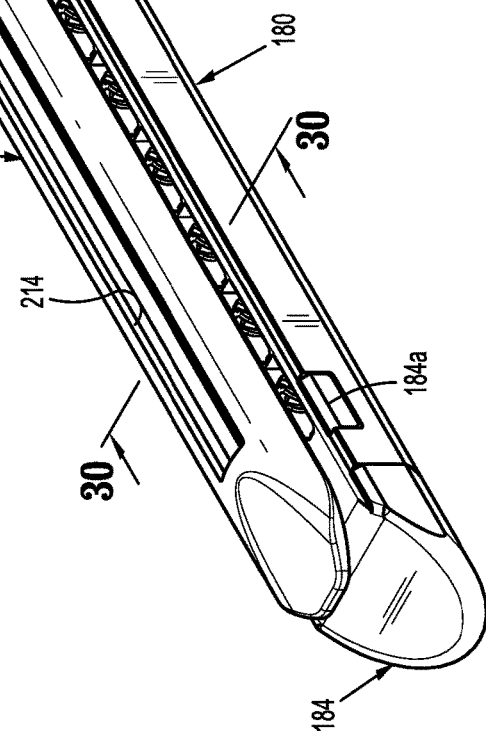
FIG. 24 is a side perspective view of the tool assembly of the stapler reload of the surgical stapler shown in FIG. 1 with the tool assembly in the approximated position prior to firing.

Referring to FIGS. 24-26, when the proximal drive member 118 (FIG. 23) is advanced via operation of the actuating device 12 (FIG. 1), the hook portion 119a (FIG. 18) of the drive member link 119 translates through the recesses 144b of the distal drive members 136a, 136b into engagement with a wall 144c defining a distal end of the recesses 144b of the distal drive members 136a, 136b. When this occurs, further distal movement of the drive member link 119 effects corresponding distal movement of the distal drive members 136a, 136b to effect distal movement of the working end 150 of the drive assembly 151.

Distal movement of the working member 150 of the drive assembly in relation to the anvil 182 advances the upper beam 152 of the working member 150 into engagement with the proximal cam surface 216 of the anvil 182. Engagement of the upper beam 152 with the proximal cam surface 216 urges the anvil 182 against the bias of the leaf spring 220 towards the cartridge body 184 to move the tool assembly 114 to the clamped or approximated position (FIG. 26). In the approximated position of the tool assembly 114, the cams 226 of the sled 189 are positioned immediately proximal of the proximal-most pushers 187.

Figure 29:
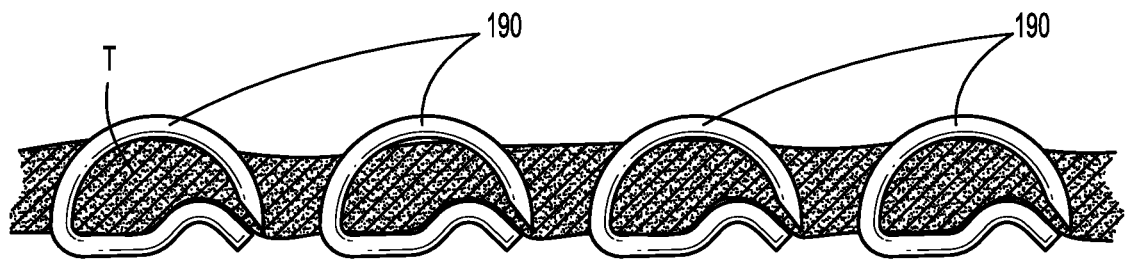
FIG. 29 is a side view of the staples of the of the tool assembly of the stapler reload of the surgical stapler shown in FIG. 1 after the staples have been formed in tissue.
Figure 30:
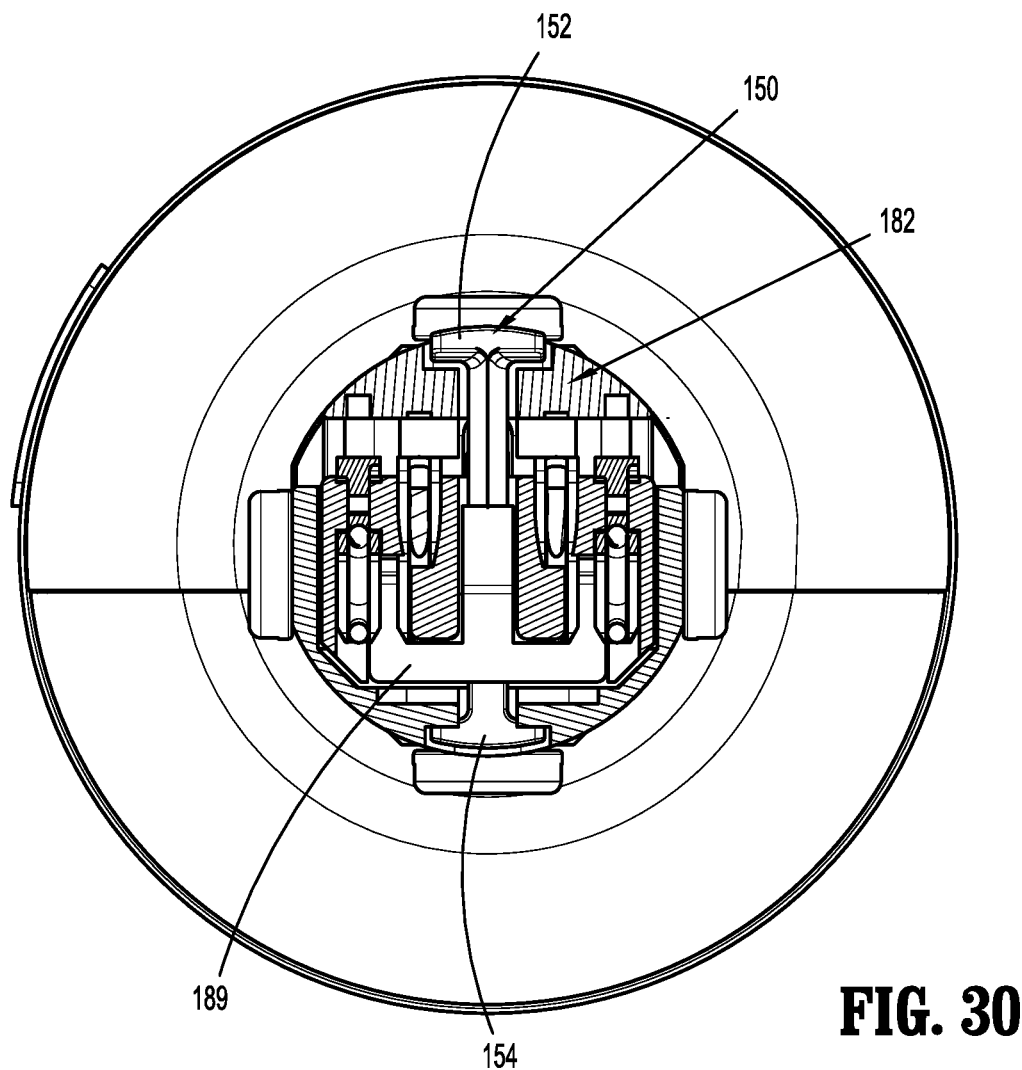
FIG. 30 is a transverse cross-sectional view through the working end of the drive member of the tool assembly shown in FIG. 27 as staples are being fired.
Figure 31:
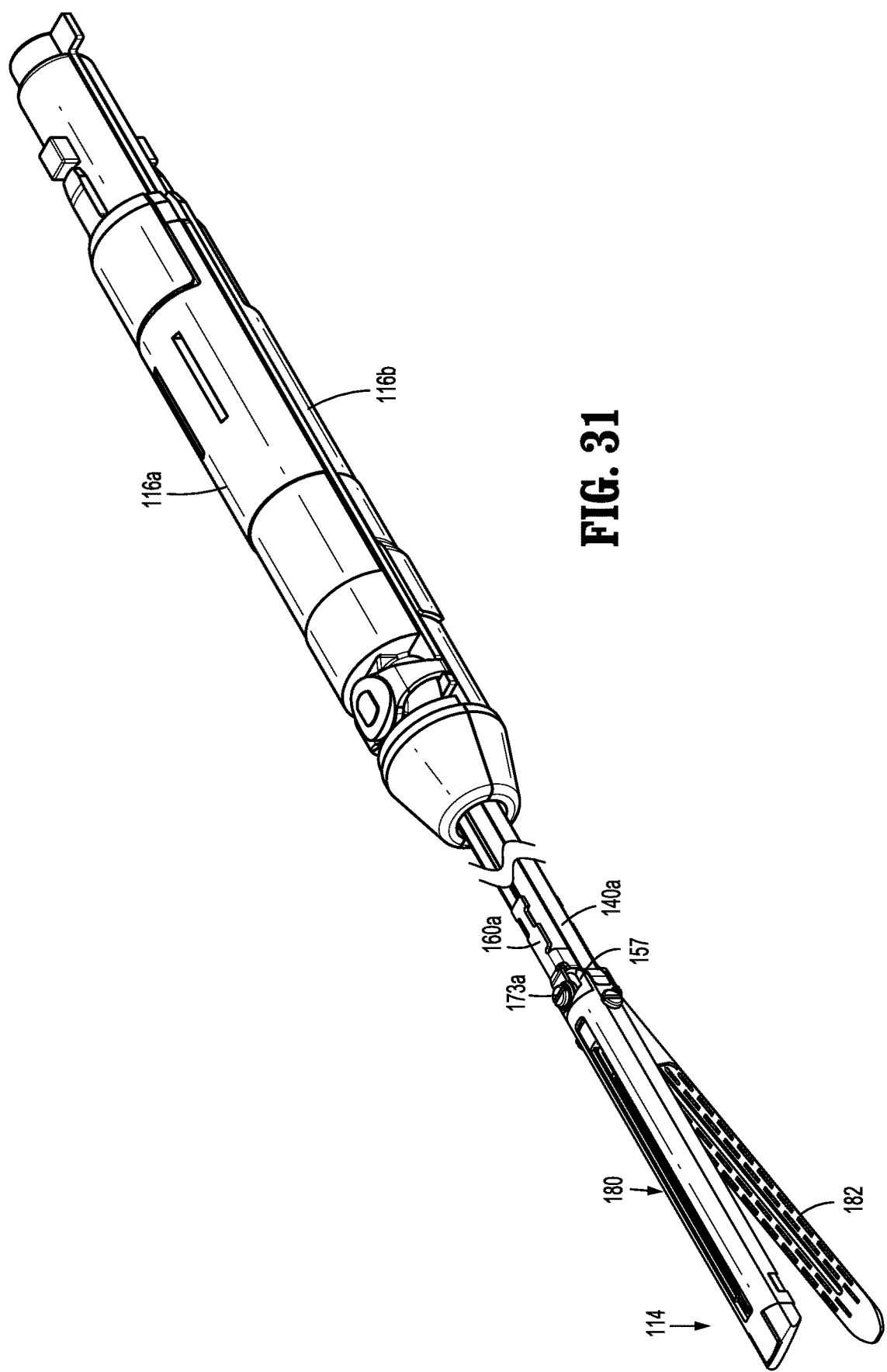
FIG. 31 is a side, perspective view of the stapler reload shown in FIG. 1A in a non-articulated and unapproximated position with the proximal tube of the proximal body portion and the shaft tube of the shaft portion removed.

Referring to FIGS. 27-30, continued advancement of the proximal drive member 118 (FIG. 23) advances the working member 150 of the drive assembly 151 through the cartridge body 184 to drive the sled 189 through the cartridge body 184. As the working member 150 advances through the cartridge body 184, the upper beam 152 engages the anvil 182 and the lower beam 154 engages the cartridge channel 186 to progressively clamp tissue as the working member 150 advances through the cartridge body 184. Movement of the sled 189 through the cartridge body 184 moves the cams 226 of the sled 189 through the channels 236 in the cartridge body 184 into sequential engagement with the pushers 187 to rotate the pushers 187 about the pivot members 244 formed within each staple pocket 240. As the pushers 187 are rotated about a respective pivot member 244 within a staple pocket 240, each staple 190 is pivoted or rotated upwardly with the respective pusher 187 to direct the tapered tip 250 of the staple 190 through tissue T into an anvil pocket 210 of the anvil 182 to initiate deformation of the staple 190 (FIG. 28). As the pusher 187 and a respective staple 190 are rotated within a staple pocket 240, the curved body 252 of the staples 190 is guided from the staple pocket 240 into the anvil pockets 210 by the circular walls 242 of the staple pockets 240. The staples 190 are configured to define a substantially D-shaped configuration when deformed (FIG. 29).

As discussed above, the deformed staples 190 are substantially D-shaped. When the tool assembly 114 is returned to the open or unclamped position by retracting the working member 150 through the cartridge body 184 after the staples 190 are fired, the staples 190 are free to be disengaged from the pivot members 244.

Referring to FIGS. 3 and 31-35, the tool assembly 114 can be articulated by movement of the articulation rods 140a, 140b in opposite directions in relation to each other. As discussed above, the articulation rods 140a, 140b extend from the proximal body portion 110 through the elongated shaft portion 112 to the tool assembly 114. A distal end of each of the articulation rods 140a, 140b is connected to the pivot member 157 by pins 172 (FIG. 3A) that extend through the distal openings 210a of the articulation rods 140a, 140b into the bores 172 of the pivot member 157. As discussed above, the proximal ends of the articulation rods 140a, 140b include cutouts 142a, 142b (FIG. 3B), respectively, that receive one side of hook portions 120a, 122a of the articulation links 120, 122, respectively, to connect the articulation links 120, 122 to the articulation rods 140a, 140b. The first and second articulation links 120, 122 are slidably supported between the housing halves 116a, 116b of the proximal body portion 110. The first articulation link 120 has a distal end connected to the articulation rods 140a and a proximal end connected to an articulation assembly 350 (FIG. 1) of the actuating device 12 (FIG. 1).

The articulation member 123 includes a C-shaped body 302 having spaced fingers 304, 306 and a central opening 308 (FIG. 32). The fingers 304, 306 are received in cutouts 310 (FIG. 3B) formed in the distal end of first and second articulation links 120 and 122. The central opening 308 receives a housing post 312 (FIG. 33) formed on housing half 116b of the central body portion 110 (FIG. 1) to rotatably support the C-shaped body 302 on the housing half-section 116b. A nut 318 is provided to secure the C-shaped body on the post 312. The nut 318 can be pressed onto the post 312. In use, movement of the first articulation link 120 in one direction as indicated by arrow "A" in FIG. 34 causes the articulation member 123 to pivot about the housing post 312 and effect movement of the second articulation link 122 in a second direction as indicated by arrow "B".

In use, when the first articulation link 120 is moved by the articulation assembly 350 (FIG. 1) of the actuating device 12 in direction A, the articulation rod 140a, which is connected to link 120 via placement of hook portion 120a in cutout 142a (FIG. 3B), is also moved in direction A. Movement of the first articulation link 120 in direction A effects pivotal movement of the articulation member 123 which causes movement of the second articulation link 122 in the direction of arrow B. Movement of the second articulation link 122 in direction of arrow B causes movement of articulation rod 140b in the direction of arrow B.

As discussed above, the distal ends of articulation rods 140a and 140b are connected to opposite sides of the pivot member 157 by pins 172. As the articulation rods 140a, 140b are moved in opposite directions, the pivot member 157 is pivoted about the pivot pin 170 to pivot the cartridge channel 186 of the cartridge assembly 180 in relation to shaft portion 112 of the reload 100. Since the cartridge channel 186 is secured to the anvil 182 and supports the cartridge body 184, pivotal movement of the cartridge channel 186 causes pivotal movement of the tool assembly 114 about the pivot pins 170 such that the longitudinal axis of the tool assembly 114 moves from a position aligned with the longitudinal axis of the shaft portion 112 (FIG. 31) to a position at an angle to the longitudinal axis of the shaft portion 112. It is noted that the distal drive members 136a, 136b are formed of a resilient material such as spring steel to facilitate movement of the drive members 136a, 136b about the axis of articulation, i.e., the axis of the pivot pin 170, to facilitate actuation of the tool assembly 114 when the tool assembly 114 is articulated.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical staple and pusher assembly comprising:
   a surgical staple having a distal leg portion and a proximal leg portion, the distal leg portion including first and second ends and a curved body extending between the first and second ends, the first end of the distal leg portion including a tapered tip, the proximal leg portion including first and second ends, the second end of the proximal leg portion including a blunt tip, the second end of the distal leg portion coupled to the first end of the proximal leg portion, wherein the distal leg portion and the proximal leg portion are configured to have a D-shaped deformed configuration; and
   a pusher including a body defining a channel and a slot, the body of the pusher having a curved outer surface configured to slide along a circular wall of a cartridge body of a stapling device, wherein the channel receives the proximal leg portion of the surgical staple to support the surgical staple on the pusher and the slot is configured to receive a pivot member to facilitate rotation of the pusher about the pivot member.

2. The surgical staple and pusher assembly of claim 1, wherein the slot is defined by a curved surface that facilitates rotation of the pusher about the pivot member.

3. The surgical staple and pusher assembly of claim 1, wherein the proximal leg portion of the surgical staple includes a recessed portion and the channel defined in the body of the pusher includes a bump that is received within the recessed portion of the surgical staple.

4. The surgical staple and pusher assembly of claim 3, wherein the pusher includes a distal end and the channel is defined in the distal end of the pusher such that the surgical staple is supported within the channel distally of the pusher.

5. A surgical stapler comprising:
   a shaft portion having a distal end portion;
   a tool assembly supported on the distal end portion of the shaft portion, the tool assembly including an anvil and a cartridge assembly, the cartridge assembly having a cartridge body defining a plurality of staple pockets and a surgical staple and pusher assembly received within each of the plurality of staple pockets, each of the plurality of staple pockets defined by a circular wall, each of the surgical staple and pusher assemblies including:
   a surgical staple having a distal leg portion and a proximal leg portion, the distal leg portion including first and second ends and a curved body extending between the first and second ends, the first end of the distal leg portion including a tapered tip, the proximal leg portion including first and second ends, the second end of the proximal leg portion including a blunt tip, the second end of the distal leg portion coupled to the first end of the proximal leg portion, wherein the distal leg portion and the proximal leg portion are configured to have a D-shaped deformed configuration; and
   a pusher including a body defining a channel, the body of the pusher having a curved outer surface supported on and movable along the circular wall of the staple pocket, wherein the channel receives the proximal leg portion of the surgical staple to support the surgical staple on the pusher; and a drive assembly having a working member that is configured to move through the tool assembly to effect rotatable movement of each of the pushers within a respective one of the staple pockets, wherein rotatable movement of each of the pushers ejects the staple from the respective staple pocket of the cartridge body.

6. The surgical stapler of claim 5, wherein the cartridge body includes a pivot member supported within each of the plurality of staple receiving slots, each of the pushers being rotatably supported on a respective one of the pivot members within a respective one of the plurality of staple receiving slots.

7. The surgical stapler according to claim 6, wherein each of the staple pockets includes a circular wall, each of the circular walls slidably supporting a respective one of the pushers.

8. The surgical stapler according to claim 5, wherein the cartridge body defines at least two rows of staple pockets and at least one channel that extends between the at least two rows of staple pockets.

9. The surgical stapler according to claim 8, further including a sled configured to translate through the at least one channel of the cartridge body, the sled including at least one cam that is positioned to sequentially engage the pushers to effect rotatable movement of the pushers within the cartridge body.

10. The surgical stapler according to claim 9, wherein the sled is positioned within the cartridge body to be engaged and advanced by the working member of the drive assembly.

11. The surgical stapler according to claim 10, wherein each of the pushers is positioned to extend into the at least one channel of the cartridge body such that translation of the sled through the at least one channel causes the at least one cam to contact the pushers in two adjacent rows of the at least two rows of staple pockets to effect rotation of the pushers.

12. The surgical stapler according to claim 11, wherein the at least two rows of staple pockets includes four rows of staple pockets and the at least one cam includes two cams.

13. The surgical stapler according to claim 5, wherein each of the staples includes a single tissue penetrating leg portion.

14. The surgical stapler according to claim 13, wherein each of the plurality of staple pockets is defined by a circular wall and the single tissue penetrating leg portion is curved and is configured to slide along the circular wall defining the respective staple pocket.

15. The surgical stapler according to claim 5, wherein the working member of the drive assembly has an I-beam configuration and includes an upper beam and a lower beam, the upper and lower beams engageable with the anvil and the cartridge assembly to progressively clamp tissue as the working member moves through the tool assembly.

16. The surgical stapler according to claim 15, wherein the cartridge assembly includes a cartridge channel that supports the cartridge body, the surgical stapler further including first and second articulation links, each of the first and second articulation links having a distal end operatively connected to a proximal end of the cartridge channel, the first and second articulation links being axially movable in opposite directions to pivot the tool assembly in relation to the shaft portion.

17. The surgical stapler according to claim 16, further including a pivotal articulation member interconnecting the first articulation link to the second articulation link, wherein pivotal movement of the articulation member causes movement of the first articulation link in one direction and effects movement of the second articulation link in an opposite direction.

18. A surgical staple and pusher assembly comprising:
a surgical staple having a distal leg portion and a proximal leg portion, the distal leg portion including first and second ends and a curved body extending between the first and second ends, the first end of the distal leg portion including a tapered tip, the proximal leg portion including first and second ends, the second end of the proximal leg portion including a blunt tip, the second end of the distal leg portion coupled to the first end of the proximal leg portion, wherein the distal leg portion and the proximal leg portion are configured to have a D-shaped deformed configuration; and
a pusher including a body defining a channel and a slot, the body of the pusher having a curved outer surface configured to slide along a circular wall of a cartridge body of a stapling device, the channel of the pusher receiving the proximal leg portion of the surgical staple to support the surgical staple on the pusher and the slot configured to receive a pivot member to facilitate rotation of the pusher about the pivot member, wherein the curved body of the distal leg of the surgical staple having a radius of curvature that corresponds to a radius of curvature of the curved outer surface of the pusher.

19. The surgical staple and pusher assembly of claim 18, wherein the slot is defined by a curved surface that facilitates rotation of the pusher about the pivot member.

* * * * *